United States Patent
Xiao et al.

(10) Patent No.: US 10,407,454 B2
(45) Date of Patent: Sep. 10, 2019

(54) DEFINED ENZYMATIC SYNTHESIS OF LIPID A ANALOGS

(71) Applicant: The Board of Trustees of the Leland Stanford Junior University, Stanford, CA (US)

(72) Inventors: Xirui Xiao, Stanford, CA (US); Chaitan Khosla, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 201 days.

(21) Appl. No.: 15/400,863

(22) Filed: Jan. 6, 2017

(65) Prior Publication Data

US 2017/0198003 A1    Jul. 13, 2017

Related U.S. Application Data

(60) Provisional application No. 62/276,028, filed on Jan. 7, 2016.

(51) Int. Cl.
| | | |
|---|---|---|
| *C07H 13/06* | (2006.01) | |
| *C12P 19/26* | (2006.01) | |
| *C12P 19/44* | (2006.01) | |

(52) U.S. Cl.
CPC .............. *C07H 13/06* (2013.01); *C12P 19/26* (2013.01); *C12P 19/44* (2013.01); *C12Y 203/0118* (2013.01); *C12Y 203/01085* (2013.01); *C12Y 203/01129* (2013.01); *C12Y 203/01191* (2013.01); *C12Y 204/01182* (2013.01); *C12Y 207/0113* (2013.01); *C12Y 305/01* (2013.01); *C12Y 306/01054* (2013.01); *C12Y 604/01002* (2013.01)

(58) Field of Classification Search
None
See application file for complete search history.

(56) References Cited

U.S. PATENT DOCUMENTS

| | | | |
|---|---|---|---|
| 2004/0213804 A1 | 10/2004 | Michon et al. | |
| 2011/0092387 A1* | 4/2011 | Monforte | C12Q 1/6809 506/9 |
| 2011/0250659 A1 | 10/2011 | Roberts et al. | |

FOREIGN PATENT DOCUMENTS

| | | |
|---|---|---|
| EP | 0172581 B1 | 5/1992 |
| WO | 2014/138696 A1 | 12/2014 |

OTHER PUBLICATIONS

Wang et al. Biol. Rev. (2015) 90: 408-427 (Year: 2015).*
Chan et al. Biochem. J. (2010) 430: 1-19 (Year: 2010).*

* cited by examiner

*Primary Examiner* — Susan M Hanley
(74) *Attorney, Agent, or Firm* — Pamela J. Sherwood; Bozicevic, Field & Francis LLP

(57) ABSTRACT

Provided herein include methods and compositions for synthesis of Lipid $IV_A$ and derivatives thereof, using a defined set of pathway enzyme, which may be isolated and used to reconstitute all or part of the pathway in a cell-free reaction.

13 Claims, 13 Drawing Sheets
(7 of 13 Drawing Sheet(s) Filed in Color)
Specification includes a Sequence Listing.

DEFINED ENZYMATIC SYNTHESIS OF LIPID A ANALOGS

CROSS REFERENCE

This application claims benefit of U.S. Provisional Patent Application No. 62/276,028, filed Jan. 7, 2016, which application is incorporated herein by reference in its entirety.

FEDERALLY SPONSORED RESEARCH AND DEVELOPMENT

This invention was made with Government support under contracts AI109662 and GM087934 awarded by the National Institutes of Health. The Government has certain rights in the invention.

BACKGROUND OF THE INVENTION

Lipid A, the hydrophobic anchor of bacterial endotoxin is not only an essential component of the outer membrane of Gram-negative bacteria, but it is also one of the most potent small molecule elicitors of the eukaryotic innate immune response. Indeed, so important is its role in innate immunity that humans have evolved multiple proteins with the capacity for high-affinity recognition of this glycolipid, including LBP, CD14, the TLR4-MD2 complex, caspase 4, and caspase 5. Notwithstanding impressive advances in total synthesis of this complex molecule, the availability of facile methods to prepare structurally defined analogs of this family of natural products remains a major roadblock in our understanding of their remarkable biological properties. Here we present a fundamentally novel approach to access these structure-activity relationships.

SUMMARY OF THE INVENTION

Compositions of isolated analogs of lipid A; and methods and compositions for the synthesis of such analogs, including cell-free synthetic methods and compositions, are provided. The methods of the invention feature reaction mixtures comprising defined sets of proteins involved in lipid synthesis pathways, including without limitation bacterial lipid synthesis pathways. In some embodiments the sets of proteins are provided in a purified or semi-purified form in ratios appropriate for high flux rate biosynthetic reactions of the desired compound. In some embodiments the set of proteins are derived from a single organism. In some embodiments the proteins are derived from multiple organisms. The synthetic reactions can be initiated with substrates acetyl-CoA, $NaHCO_3$, isovaleryl-CoA, malonyl-CoA, etc., and UDP-N-acetylglucosamine (UDP-GlcNAc). Various fatty acyl chains can be provided as substrates.

Lipid A analogs of the present invention include compounds having the structure of Formula I:

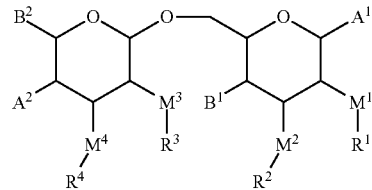

(a) wherein M1, M2, M3, M4 each are independently NH or O; at least one of $R^1$, $R^2$, $R^3$, $R^4$ is selected, independently, from the following structure:

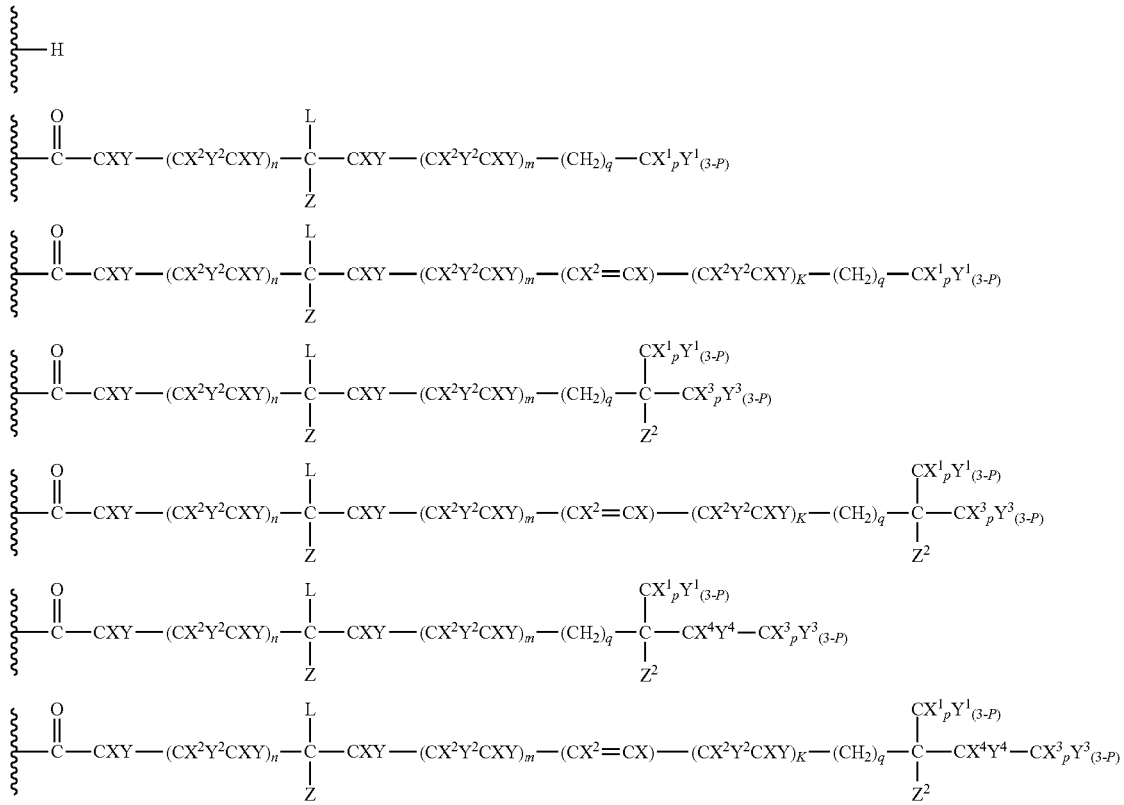

-continued
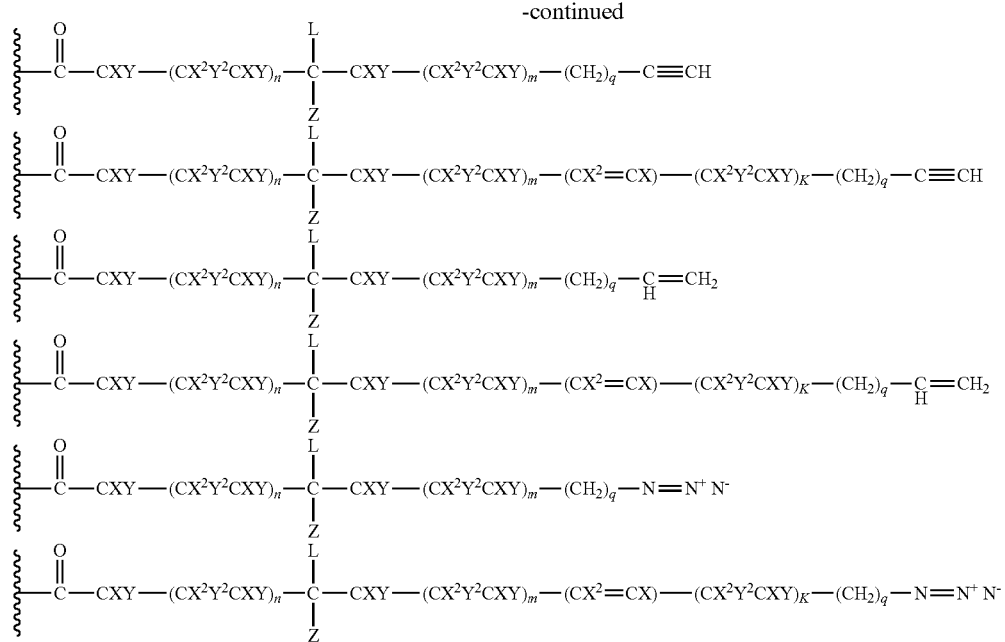
wherein each X, Y, Z, $X^1$, $Y^1$, $Z^1$, $X^2$, $Y^2$, $Z^2$, $X^3$, $Y^3$, $X^4$, $Y^4$ are, independently, H, D, F, Cl, Br; each m, n, q and k are, independently, integers from 0 to 30; each p is independently an integer from 0 to 3; L is independently selected from the following structure:
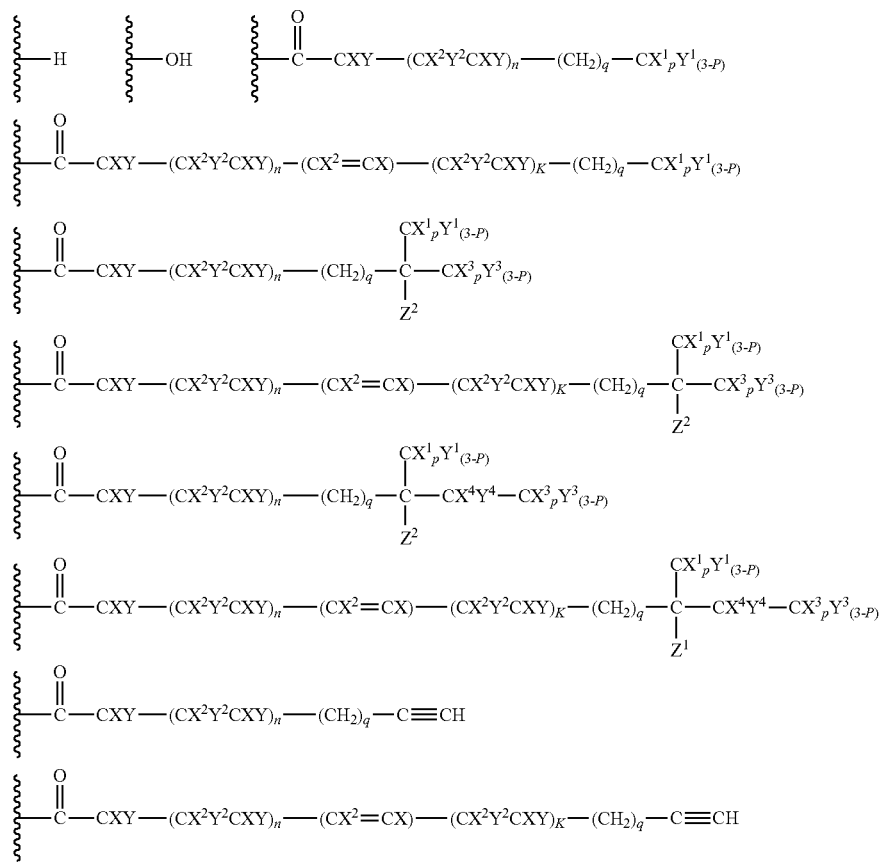

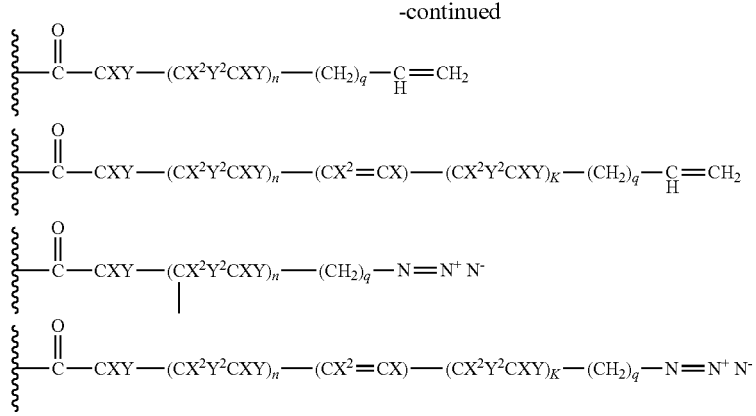

wherein each $X, Y, Z, X^1, Y^1, Z^1, X^2, Y^2, X^3, Y^3, X^4, Y^4$ are, independently, H, D, F, Cl, Br; each m, n and k are, independently, integers from 0 to 30; each p is independently an integer from 0 to 3.

(b) wherein at least one of $A^1$, $A^2$ is selected, independently, from the following structure:

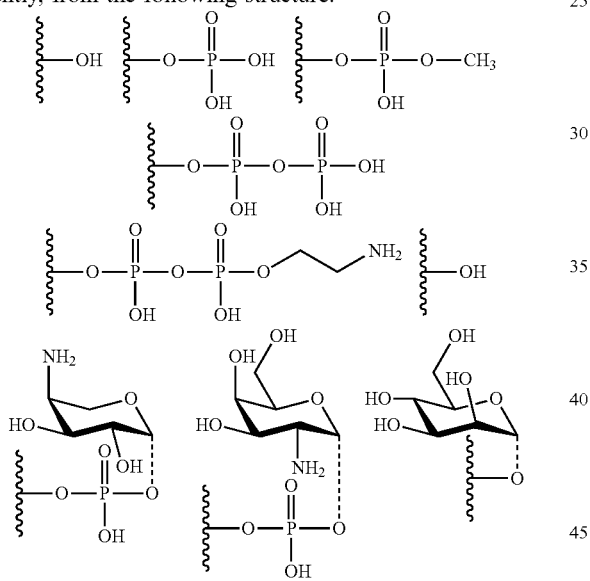

and (C) wherein at least one of $B^1$, $B^2$ is selected, independently, from the following structure:

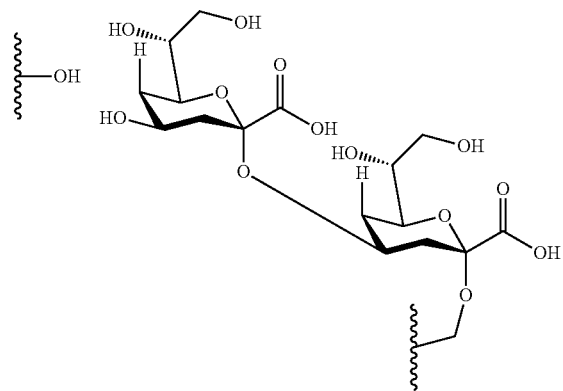

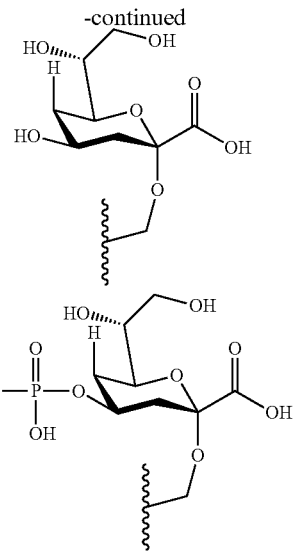

By substituting halogenated or isotope labeled (D, F, Cl, Br, I) substrates, the in vitro system can incorporate those elements into fatty acyl chains. Depending on where the substrate is labeled, the exogenous elements can appear on every or every other carbon. If the substrate, for example, is terminal alkyne short chain acyl-CoA, the triple bond CC will be incorporated. The substrate unit can also be iso- or anteiso-branched chain acyl-CoA, thus leading to incorporation of a corresponding branched unit.

In some embodiments, a Lipid A analog of the invention has a structure of Formula 6a, 6b, 6c, 6d or 6e, as shown in FIG. 1.

In some embodiments, one or both of $A^1$ and $A^2$ is $CO_2H$, where the modification may be introduced via chemical modification of the enzymatically generated compound.

In some embodiments of the invention, a compound of Formula I, including specifically compounds 6a-6e, is provided. In some embodiments the compound of Formula I is synthesized by a defined set of enzymes. In some embodiments the defined set of enzymes is provided in a cell-free reaction mixture, where the reaction mixture can further comprise co-factors, buffers, etc. as required for biosynthesis, including without limitation ATP, $MgCl_2$, NADPH, and the like. In some embodiments a set of polynucleotides encoding pathway enzymes is introduced into a bacterial cell, where expression of the enzymes may be coordinately regulated.

In some embodiments a compound of Formula I is provided as a pharmaceutical composition, e.g. in combination with a pharmaceutically acceptable excipient. In some embodiments the pharmaceutical composition is provided in a unit dose formulation, e.g. a dose effective to achieve the desired biological effect when administered to an individual, e.g. antagonism of lipid A, agonists of TLR4, etc., depending on the specific analog that is selected.

In some embodiments, methods of use for compounds of Formula I are provided. Methods of use include without limitation antagonism or agonism of TLR4. In certain embodiments, compounds that are Lipid A antagonists find use in treatment of conditions including sepsis and septic shock, and as protection against certain viral infections, including without limitation influenza infection. In some embodiments TLR4 agonists, i.e. compounds that agonize or mimic Lipid A activity, are useful as immunomodulators, adjuvants, etc., for methods in which an enhanced immune response is desired, including without limitation vaccination methods, where the target antigen can be a virus, bacteria, protozoan, etc., or can be a self-antigen, including cancer-associated antigens.

The biosynthetic pathway of Lipid $IV_A$ and analogs can be operationally divided into four modules, shown in FIG. 1. Module A, comprised of AccC, AccA, AccD, and holo-AccB converts acetyl-CoA into malonyl-CoA. Module B, comprised of FabH, FabD, FabG, FabA or FabZ, FabI, and holo-ACP, which harbors a tethered phosphopantetheine arm, converts acetyl-CoA and malonyl-CoA to a fatty acyl chain. Module C, comprised of FabB or FabF, FabD, FabG, FabA or FabZ, and FabI, converts malonyl-CoA and the butyryl-ACP thioester product of module B to elongate the fatty acid chains. Module D, comprised of LpxA, LpxC, LpxD, LpxH, LpxB, and LpxK, converts the 3-hydroxy-myristoyl-ACP intermediate and UDP-N-acetylglucosamine (UDP-GlcNAc) into Lipid $IV_A$ and analogs thereof.

In some embodiments, all of the enzymes in Modules A-D are purified and introduced into a reaction mixture. Each enzyme can be from the same or a different organism, including without limitation the enzymes set forth in Table B. In other embodiments, the enzymes in a Module are replaced with the product of that module. A reaction mixture may comprise Module A-D, comprising as substrates acetyl-CoA and UDP-GlcNAc, with co-factors $MgCl_2$, ATP and NADPH. A reaction mixture may comprise Modules B-D, comprising as substrates malonyl-CoA, acetyl-CoA and UDP-GlcNAc, with co-factors ATP and NADPH. A reaction mixture may comprise Modules C-D, comprising as substrates malonyl-CoA and butyryl-ACP thioester. A reaction mixture may comprise Module D, comprising as substrates 3-hydroxymyristoyl-ACP intermediate and UDP-N-acetyl-glucosamine (UDP-GlcNAc). In addition to acetyl-CoA, other groups can be included in the reaction mixture, including without limitation isovaleryl-CoA as an intermediate for branched chain fatty acids, etc. Suitable salts and buffers may be provided, for example and without limitation, $Mg^{++}$ at a concentration of from about 1 mM to about 50 mM, about 5 mM to about 25 mM; and a sodium phosphate buffer to maintain a neutral pH. Reducing agents (e.g., TCEP) may also be added at concentrations from about 1 mM to about 10 mM, for example from about 2.5 mM to about 10 mM, from about 5 mM to about 10 mM, from about 7.6 mM to about 10 mM, from about 2.5 mM to about 5 mM, from about 5 mM to about 7.5 mM, from about 5 mM to about 10 mM, from about 7.5 mM to about 10 mM.

In some embodiments of the invention, the enzymes are provided in the molar ratios 10:5:1, holo-AccB and holo-ACP:Module D enzymes:all other enzymes. In other embodiments, a molar excess is provided of at least about 2-fold, about 3-fold, about 4-fold, about 5-fold about 7 fold, about 10-fold or more of the Module D enzymes in relation to the Module A, B and C enzymes (when present) except holo-AccB and holo-ACP, which can be provided in a molar ratio equivalent to the Module D enzymes, or in excess of the Module D enzymes, e.g. at about a 1.5-fold excess, about 2-fold excess, about 2.5-fold excess, about 3-fold excess, about 4-fold excess, about 5-fold excess.

The cell free reaction mixtures of the invention can provide for highly efficient synthesis of the desired lipids, e.g. a yield of about 10%, about 25%, about 50%, about 75% or more yield on an acetyl-CoA basis.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE EMBODIMENTS

Figure 1:
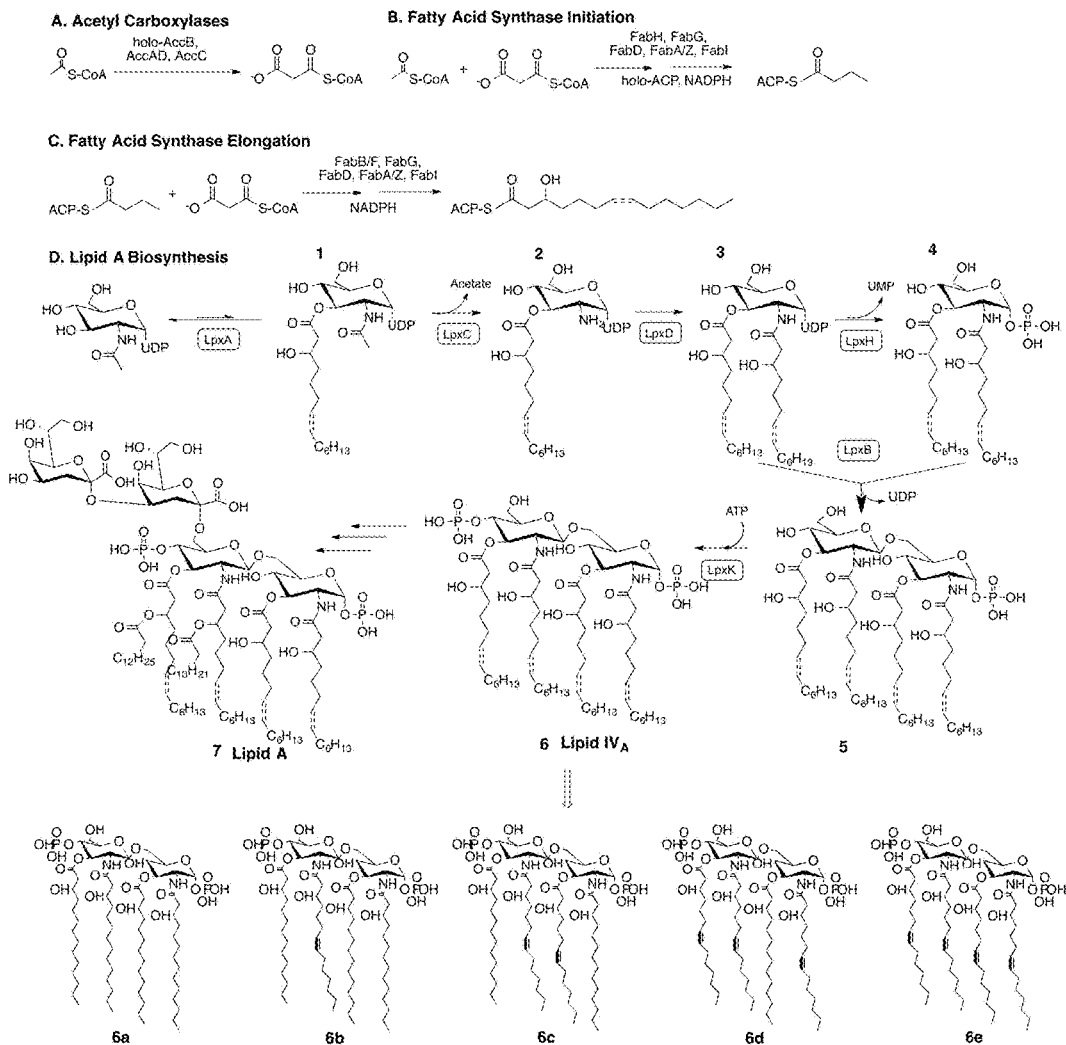
FIG. 1. In vitro enzymatic synthesis of Lipid $IV_A$ (A) Acetyl-CoA Carboxylase: In the presence of holo-ACP and sodium bicarbonate, acetyl-CoA is carboxylated to form malonyl-CoA in situ. (B) Fatty Acid Synthase Initiation: Catalyzed by FabD, FabH, FabA, FabZ abd FabI, acetyl-CoA and malonyl-CoA undergo condensation and subsequent reduction to form butyryl-ACP. (C) Fatty Acid Synthase Elongation: Butyryl-ACP is extended via 5 rounds of analogous reactions to produce 3-hydroxy-myristoyl-ACP that is either fully saturated or monounsaturated. These extension cycles are catalyzed by either the ketosynthase FabB or FabF in collaboration with FabD, FabG, FabA or FabZ, and FabI. (D) Lipid $IV_A$ Biosynthesis: Two equivalent of 3-hydrpxymyrystoyl moieties are trans-acylated onto the sugar nuclrotide UDP-GlcNAc to form the intermediate UDP-2,3-diacylglycosamine (3), which is then hydrolyzed at the pyrophosphate bond to form Lipid X (4). UDP-2,3-diacylglycosamine and Lipid X undergo condensation to generate mono-phosphoryl Lipid $IV_A$ The final phosphorylation at the 4' position on the disaccharide backbone forms Lipid $IV_A$.

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. As used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The present inventions have been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

A "therapeutically effective amount" means the amount that, when administered to a subject for treating a disease, is sufficient to effect treatment for that disease.

Acetyl-CoA carboxylase refers to enzymes capable of carboxylating acetyl-CoA to form malonyl-CoA. These enzymes include but are not limited to AccA, holo-AccB, AccC and AccD.

Chain initiating enzymes of fatty acid synthases refer to enzymes capable of priming the acyl-carrier protein (ACP) with coenzyme A-bound substrates and catalyzing the first cycle of fatty acid elongation. These enzymes include but are not limited to FabB or FabF, FabD, FabG, FabA or FabZ, and FabI.

Chain elongating enzymes of fatty acid synthases refer to enzymes capable of further elongating the ACP-bound product of the chain initiating enzymes of fatty acid synthases. These enzymes include but are not limited to FabF, FabD, FabG, FabA or FabZ, and FabI.

Lipid A biosynthetic enzymes, including but not limited to LpxA, LpxC, LpxD, LpxH, LpxB, and LpxK, refer to enzymes capable of introducing acyl chains or phosphate groups on selected positions of nucleotide sugar.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or linear saturated hydrocarbon group (i.e., a mono-radical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "C1-C6 alkoxy" or "lower alkoxy" herein may, for example, may contain 1 to 3 carbon atoms, and as a further example, such substituents may contain 1 or 2 carbon atoms (i.e., methoxy and ethoxy).

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—CH2-), ethylene (—CH2CH2-), propylene (—CH2CH2CH2-), 2-methylpropylene (—CH2-CH(CH3)-CH2-), hexylene (—(CH2)6-) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —NRR' wherein R and R' are independently hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

As used herein, the terms "Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO— heteroaryl, —SO$_2$-alkyl, —SO$_2$-substituted alkyl, —SO$_2$-aryl, —SO$_2$-heteroaryl, and fused heterocycle.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH2), mono-substituted C1-C24 alkylcarbamoyl (—(CO)—NH(C1-C24 alkyl)), di-substituted alkylcarbamoyl (—(CO)—N(C1-C24 alkyl)2), mono-substituted arylcarbamoyl (—(CO)—NH-aryl), thiocarbamoyl (—(CS)—NH2), carbamido (—NH—(CO)—NH2), cyano (—C≡N), isocyano (—N+≡C—), cyanato (—O—C≡N), isocyanato (—O—N+≡C—), isothiocyanato (—S—C≡N), azido (—N=N+=N—), formyl (—(CO)—H), thioformyl (—(CS)—H), amino (—NH2), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR=NH where R=hydrogen, C1-C24 alkyl, C5-C20 aryl, C6-C20 alkaryl, C6-C20 aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO2), nitroso (—NO), sulfo (—SO2-OH), sulfonato (—SO2-O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO2-alkyl), C5-C20 arylsulfonyl (—SO2-aryl), phosphono (—P(O)(OH)2), phosphonato (—P(O)(O-)2), phosphinato (—P(O)(O—)), phospho (—PO2), and phosphino (—PH2), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a bivalent radical moiety that connects two groups via covalent bonds. Examples of such linking groups include alkylene, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), carbonyldioxy (—O—CO—O—), alkyldioxy (—O—(CH2)n-O—), epoxyimino (—O—NH—), epimino (—NH—), carbonyl (—CO—), etc. Any convenient orientation and/or connections of the linkers to the linked groups may be used.

When the term "substituted" appears prior to a list of possible substituted groups, it is intended that the term apply to every member of that group. For example, the phrase "substituted alkyl and aryl" is to be interpreted as "substituted alkyl and substituted aryl."

In certain embodiments, a substituent may contribute to optical isomerism and/or stereoisomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include 1H, 2H (i.e., D) and 3H (i.e., T), and reference to C is meant to include 12C and all isotopes of carbon (such as 13C).

Definitions of other terms and concepts appear throughout the detailed description below.

The nucleic acids and proteins used to practice this invention, whether RNA, DNA including genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids or polypeptides can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Host cells of interest for pathway engineering, or as a source of enzymes include a wide variety of heterotrophic and autotrophic microorganisms, including bacteria, fungi and protozoans. Species of interest include, without limitation, gram negative bacteria, e.g. members of the enterobacteriacae, those set forth in Table B, etc.

Techniques for the manipulation of nucleic acids and recombinant production of proteins are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Flux. The term "flux" as used herein refers to the rate that molecules pass through a pathway or reaction of interest. Among the factors that control flux are rate of catalysis of enzymes in the pathway, the availability of substrate, the concentration of enzymes in a cell, the proximity of enzymes in a pathway, etc. Methods of determining flux rates are known and used in the art, for example as described by Wiechert et al. (2001) Metab. Eng. 3, 265-283, A universal framework for 13C metabolic flux analysis", and Metab Eng. 2001 July; 3(3):195-206; or metabolic engineering texts such as Lee and Papoutsakis, 1999, Stephanopoulos, Aristidou, Nielsen, 1998, Nielsen and Eggeling, 2001, each herein specifically incorporated by reference. Flux may be calculated from measurable quantities using techniques such as metabolic flux analysis (MFA), for example by direct measurement of the conversion of isotopically labeled substrate.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, µ-galactosidase, luciferase, etc.; and the like.

Enzyme Pathway: As used herein, the term "enzyme pathway" or "pathway of interest" refers to a cellular system for converting a substrate to a product of interest, where the system comprises a plurality of enzymes and may additionally comprise substrates acted upon by one or more of the enzymes, products of the enzyme-catalyzed reaction, co-factors utilized by the enzymes, and the like. In particular reference is made to the pathway enzymes of Modules A-D described herein. The system may be present in an intact cell, or in a lysate of a cell. Many metabolic pathways are known and have been described in microbial systems, and are accessible in public databases. For example, a number of reference books are available, including, inter alia, The Metabolic Pathway Engineering Handbook (2009), ed. C. Smolke, CRC, ISBN-10: 1420077651 and 1439802963; Metabolic Engineering: Principles and Methodologies (1998) Stephanopoulos, Academic Press ISBN-10: 0126662606, Greenberg D M. Metabolic Pathways: Energetics, tricarboxylic acid cycle, and carbohydrates. Academic Press; 1967; Greenberg M. Metabolic pathways. Academic Press; 1968; Greenberg D M. Metabolic pathways. Academic; 1970; and Greenberg D M, Vogel H Within a pathway, enzymes will vary in turnover rate and the effectiveness with which a product is produced. As a result, certain enzymes in a pathway become rate-limiting. Increasing the concentration of rate-limiting enzymes in a pathway (relative to non-rate limiting enzymes) allows increased flux through the pathway of interest. The enzymes of Module D, holo-AccB and holo-ACP can be provided in molar excess relative to the other pathway enzymes.

Enzymes in a pathway may be naturally occurring, or modified to optimize a characteristic of interest, e.g. substrate specificity, reaction kinetics, solubility, codon usage, etc. In some embodiments the complete pathway comprises enzymes from a single organism, however such is not required, and enzymes can be combined from multiple organisms. For some purposes a pathway is expressed in a host cell, but such is also not required, and a complete pathway or components of a pathway may be reconstituted in a cell-free reaction. Where the system is provided in an intact cell, generally the complete set of enzymes required for pathway conversion will be present in the cell. For purposes of cell-free production, one or more enzyme modules as described herein are added to the reaction mixture so as to complete the pathway.

In the pathway system, a first substrate (S1), e.g. acetyl CoA, valeryl-CoA, butyryl-ACP thioester, UDP-GlcNAc, etc. is acted upon by a pathway entry enzyme, and is converted to a first product, although it will be understood by one of skill in the art that an enzyme may act upon more than one substrate simultaneously, and may produce more than one product, such that two or more pathways may be interconnected at a single enzyme. The first product is a substrate (S2) for downstream enzyme E2, and is converted to a second product. Depending on the complexity of the pathway, the second product may be the final product (PF), or may be a substrate (S3) for a third downstream enzyme (E3), and is converted to a third product, which may be a substrate (S4) for a fourth enzyme, etc. The final enzyme in the pathway produces the product of interest. It is a characteristic of enzyme pathways that the product of one enzyme is the substrate for the next enzyme. Products may be stable or relatively labile, but in general the final product is sufficiently stable that it can be isolated from the cell or reaction mixture.

"Cell-free system," as used herein, is an isolated cell-free system containing a defined set of enzymes that, when provided with a substrate of interest and relevant co-factors, results in the preferential generation of a compound of interest. A compound of interest is typically a chemical entity (e.g., a small molecule), particularly a compound of Formula I, which can be used as an active pharmaceutical ingredient (API), chemical precursor, or intermediate, etc.

"Substrate," as used herein, is a compound or mixture of compounds capable of providing the required elements needed to synthesize a compound of interest.

"Reducing equivalent," as used herein, is a chemical species that transfers the equivalent of one electron in a redox reaction. Examples of reducing equivalents are a lone electron (for example in reactions involving metal ions), a hydrogen atom (consisting of a proton and an electron), and a hydride ion (:H—) which carries two electrons (for example in reactions involving NAD). A "reducing equivalent acceptor" is a chemical species that accepts the equivalent of one electron in a redox reaction.

Metabolite. A metabolite is any substance produced during metabolism. For the purposes of the present invention, a metabolite is often, although not always, the product of an enzyme in the pathway of interest.

Inducible expression. The methods of the invention may make use of regulated expression of various coding sequences, including without limitation the sequences encoding pathway enzymes. Expression may be regulated by various cues, for example induction by chemicals, change of growth phase, depletion of a nutrient, temperature shifts, light, etc. In some embodiments inducible promoters regulated by the presence of an inducing agent, e.g. a chemical such as lactose, arabinose, tetracycline, etc., as known in the art.

Expression and cloning vectors usually contain a promoter that is recognized by the host organism and is operably linked to the coding sequence of interest. Promoters are untranslated sequences located upstream (5') to the start codon of a structural gene that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. While the native promoter may be used, for most purposes heterologous promoters are preferred, as they generally permit greater transcription and higher yields.

LPS, Lipid A and therapeutic uses. As a major constituent of the outer membranes of infectious gram-negative bacteria, lipopolysaccharide (LPS) triggers many pathophysiological events. Most of the toxic properties of LPS can be attributed to the hydrophobic fatty-acylated disaccharide lipid A portion of the molecule. In both in vitro and in vivo systems, LPS-sensitive cells such as monocytes and macrophages can be stimulated by LPS or lipid A to release cytokines such as tumor necrosis factor alpha (TNF-α), interleukin 1 (IL-1), IL-6, and other mediators. In vivo, release of pathophysiological concentrations of these cytokines and cellular mediators can lead to tissue damage. For this reason, a variety of therapeutic interventions have been undertaken to block the action of endotoxin and the sequelae of cellular activation by endotoxin. These approaches include administration of anti-lipid A antibodies, anticytokine antibodies, or soluble neutralizing receptors for cytokines or antagonism of cytokine receptors. Certain lipid A derivatives can inhibit the acute inflammatory response to LPS and can be useful for treatment of LPS-induced shock or mortality.

In humans, TLR4 and MD2 exist as dimers (TLR4/MD2), and LPS binding to MD2 results in the formation of the TLR4/MD2/LPS complex (2:2:2 complex). The lipid chains in LPS are located in the hydrophobic pocket of MD2, and two phosphate groups in lipid A engage in favorable interactions with positively-charged residues in TLR4 and MD2, inducing complex formation. In human cells, the presence of two phosphate and acyloxyacyl groups is necessary to activate fully TLR4-MD-2. Species-specificities exist among lipid A and its analogs. For example, lipid $IV_A$, a tetra-acylated precursor of lipid A, is a weak agonist of TLR-4-MD-2 activity in mouse, while it shows antagonistic activity in human.

Lipid $IV_A$ is an antagonist of the TLR4 receptor in human cells. Synthetic analogs are known in the art, including, for example, E5531 and E5564. Lipid A agonists have been shown to be protective for lethal influenza infection, presenting Toll-like receptors as a drug target for antiviral therapy. It is also possible to prepare lipid A analogs by combining different biosynthetic enzymes from different bacterial species. As seen in the $Kdo_2$-lipid A molecule from *E. coli*, there are two phosphate groups, and the existence of these two phosphate groups is important for TLR4/MD2 activation. While lipid A itself is too toxic when there are two phosphate groups present, monophospholipid A (MPLA) can be prepared and used as an adjuvant, as MPLA partially activates TLR4/MD2. Some bacterial species, such as *Francisella tularensis*, produce lipid A devoid of phosphate groups. These species contain extra enzymes, including LpxE and LpxF, that function as phosphatases to get rid of the phosphate groups in lipid A.

Biosynthetic enzymes from different species can be used to prepare lipid A analogs in vitro. For example, PagL and LpxR exist in *Salmonella* species and function as lipases. These enzymes function in *E. coli*, and modified lipid A species are produced by cultured bacterial cells. The repertoire of lipid A modifying enzymes from various bacterial species allows the production of lipid A analogs with beneficial activities.

Certain analogs of lipid A are TLR4 agonists, which can be used as immunomodulators and adjuvants. The agents can be formulated alone, or in combination with, for example, alum, emulsions, saponins, liposomes, and the like. TLR4 agonists can modulate innate immune responses directly in order to improve the magnitude and duration of adaptive immune responses to vaccine antigens. The agonists can be coadministered with different vaccine preparations to generate enhanced immune responses.

Production Methods

High yield synthesis of a product of interest is accomplished by providing a pathway system comprising pathway enzymes, substrates, co-factors and such salts, buffers, etc. as are required for enzyme activity. The methods of the invention provide for high yields of the desired product, which yield is greater than the yield that can be achieved with a native microbial host.

The synthetic process can be performed in a single reaction, i.e. from acetyl-CoA and/or valeryl-Co-A and UDP-GlcNAc to the final product; can be performed with different enzyme modules in different reactions, or can use chemically or purchased reagents as starting materials for synthesis with one or more of Modules B-D, Modules C-D, or Module D. The reaction can also take place sequentially by allowing one set of reactions to proceed in one vessel and then passing the supernatant through a second vessel. The enzymes of the pathway can be engineered to manipulate their activity or otherwise optimized using molecular biology, biochemistry, or similar techniques. The enzymes can be free in solution, or immobilized on a bead or other solid substrate. The methods can also be practiced with intact cells or cell lysates.

For example, and without limitation, the sets of enzymes may be as follows: Module A, comprised of AccC, AccA, AccD, and holo-AccB; Module B comprised of FabH, FabD, FabG, FabA or FabZ, FabI, and holo-ACP; Module C, comprised of FabB or FabF, FabD, FabG, FabA or FabZ, and FabI; and Module D, comprised of LpxA, LpxC, LpxD, LpxH, LpxB, and LpxK. Alternatively or in combination a set of modifying enzymes may be used, comprising: KdtA, LpxE, LpxF, LpxL, LpxM, PagP, PagL, LpxT, LpxR, ArnT, EptA, EptB, LmtA, RgtA, RgtB, and RgtC. The reaction mixture may further comprise Acetyl-CoA or an analog thereof including without limitation valeryl-CoA, UDP-GlcNAc; various carbohydrates including without limitation CMP-kdo and 4-amino-4-deoxy-alpha-L-arabinopyranosyl undecaprenyl phosphate; phospholipids including without limitation 1-palmitoyl-2-acyl-sn-glycero-3-phosphocholine, diacylglycerol diphosphate, phosphoethanolamine; and cofactors and buffers required for synthesis.

In other embodiments, the reaction can be initiated with lipid $IV_A$ and acyl-ACP, which can be generated by Sfp or *vibrio harveyi* ACP synthetase. *Vibrio harveyi* acyl-ACP synthetase catalyzes an acylation reaction of the thiol group on holo-ACP from free fatty acid ranging from 8-18 carbons. To generate various acyl-ACP, a reaction containing 200 μM of free fatty acid, such as myristic or palmitic acid, 100 μM of holo-ACP and 10 μM AasS, supplied with 1 mM ATP, 5 mM $MgCl_2$ and 1 mM TCEP is incubated in 100 mM sodium phosphate buffer overnight at room temperature. Acyl-ACP species can be further purified using ion exchange or reverse phase chromatography if purity is desired. To synthesize penta- or hexa-acylated lipid A analogues, 50 μM of lipid $IV_A$, 150 μM of acyl-ACP species with appropriate chain lengths, and the late stage transferases such as LpxL, LpxM and PagP are added into buffer for incubation at room temperature. Reaction mixtures can be directly analyzed on a mass spectrometer to determine the structure of the resulting analogues. See, for example, Yu et al. (2011) Proc Natl Acad Sci USA 108: 18643-8; and Xiao et al. (2013) Biochemistry 52: 8304-12, each herein specifically incorporated by reference.

Certain enzymes from naturally occurring Lipid A pathways in Gram-negative bacteria are of special interest based on their ability to install atypical modifications on the Lipid IV$_A$ scaffold. These enzymes are of particular utility in the generation of novel chemotypes through enzymatic mix-and-match approaches, which enzymes are listed in Table B.

TABLE B

| Enzyme | Function | EC Number | Bacteria | Uniprot Entry |
| --- | --- | --- | --- | --- |
| KdtA | lipid IVA 3-deoxy-D-manno-octulosonic acid transferase | 2.4.99.12 | *Escherichia coli* (strain K12) | P0AC75 |
| LpxE | Lipid A 1-phosphatase | 3.1.—.— | *Moraxella catarrhalis* | D5VD80 |
| | | | *Rhizobium etli* (strain CFN 42/ATCC 51251) | Q2K2U9 |
| | | | *Porphyromonas gingivalis* (strain ATCC 33277/DSM 20709/JCM 12257) | B2RLI7 |
| LpxF | Lipid A 4'-phosphatase | 3.1.—.— | *Helicobacter pylori* (strain J99/ATCC 700824) (*Campylobacter pylori* J99) | Q9ZN40 |
| | | | *Rhizobium etli* (strain CFN 42/ATCC 51251) | Q2KA78 |
| | | | *Porphyromonas gingivalis* (strain ATCC 33277/DSM 20709/JCM 12257) | B2RI48 |
| | | | *Helicobacter pylori* (strain J99/ATCC 700824) (*Campylobacter pylori* J99) | Q9ZJ31 |
| | | | *Bacteroides thetaiotaomicron* (strain ATCC 29148/DSM 2079/NCTC 10582/E50/VPI-5482) | Q8A6M3 |
| LpxL | Lipid A biosynthesis lauroyltransferase | 2.3.1.241 | *Escherichia coli* (strain K12) | P0ACV0 |
| | | | *Moraxella catarrhalis* (strain RH4) | D5VBR7 |
| | | | *Hafnia alvei* ATCC 51873 | G9Y3H2 |
| | Lipid A biosynthesis myristoyltransferase | 2.3.1.243 | *Proteus mirabilis* ATCC 29906 | C2LFR4 |
| | Lipid A biosynthesis palmitoleoyltransferase | 2.3.1.242 | *Proteus mirabilis* ATCC 29906 | C2LM44 |
| | | | *Yersinia pestis* | A0A0B6NZY9 |
| LpxM | Lipid A biosynthesis myristoyltransferase | 2.3.1.243 | *Escherichia coli* (strain K12) | P24205 |
| | | | *Hafnia alvei* ATCC 51873 | G9Y294 |
| | | | *Yersinia pestis* | Q7CIC3 |
| LpxA | Acyl-[acyl-carrier-protein]-UDP-N-acetylglucosamine O-acyltransferase | 2.3.1.129 | *Pseudomonas aeruginosa* (strain ATCC 15692/PAO1/1C/PRS 101/LMG 12228) | Q9X6P4 |
| | | | *Helicobacter pylori* (strain ATCC 700392/26695) (*Campylobacter pylori*) | O25927 |
| | | | *Moraxella catarrhalis* | Q3BDJ0 |
| LpxD | UDP-3-O-acylglucosamine N-acyltransferase | 2.3.1.— | *Pseudomonas aeruginosa* (strain ATCC 15692/PAO1/1C/PRS 101/LMG 12228) | Q9HXY6 |
| | | | *Helicobacter pylori* (strain ATCC 700392/26695) (*Campylobacter pylori*) | O24991 |
| | | | *Moraxella catarrhalis* | D5VAW6 |
| LpxT | Lipid A 1-diphosphate synthase | 2.7.4.29 | *Escherichia coli* (strain K12) | P76445 |
| LpxR | N/A | N/A | *Salmonella typhimurium* | Q0QMQ4 |
| PagL | Lipid A deacylase PagL | 3.1.1.77 | *Pseudomonas aeruginosa* (strain ATCC 15692/PAO1/1C/PRS 101/LMG 12228) | Q9HVD1 |
| PagP | Lipid A palmitoyltransferase PagP | 2.3.1.— | *Escherichia coli* (strain K12) | P37001 |
| | | | *Proteus mirabilis* (strain HI4320) | B4EYA9 |
| ArnT | Undecaprenyl phosphate-alpha-4-amino-4-deoxy-L-arabinose arabinosyl transferase | 2.4.2.43 | *Escherichia coli* (strain K12) | P76473 |
| | | | *Pseudomonas aeruginosa* (strain ATCC 15692/PAO1/1C/PRS 101/LMG 12228) | Q9HY61 |
| | | | *Bordetella pertussis* | |
| EptA | Phosphoethanolamine transferase EptA | 2.7.—.— | *Escherichia coli* (strain K12) | P30845 |
| | | | *Campylobacter jejuni* | A0A0E1EWJ6 |
| EptB | Phosphoethanolamine transferase EptB | 2.7.—.— | *Escherichia coli* (strain K12) | P37661 |

TABLE B-continued

| Enzyme | Function | EC Number | Bacteria | Uniprot Entry |
|---|---|---|---|---|
| LmtA | Lipid A methyltransferase | N/A | *Leptospira interrogans* | Q4FAC7 |
| RgtA | GalA transferase | N/A | *Rhizobium leguminosarum* | Q20DQ4 |
| RgtB | GalA transferase | | *Rhizobium leguminosarum* | Q20DQ3 |
| RgtC | GalA transferase | | *Rhizobium leguminosarum* | Q20DQ2 |

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose.

The reactions may be of any volume, either in a small scale, usually at least about 0.05 ml and not more than about 5 ml, or in a scaled up reaction, where the reaction volume is at least about 5 ml, usually at least about 50 ml, more usually at least about 100 ml, and may be 500 ml, 1000 ml, or greater up to many liters of volume. Reactions may be conducted at any scale.

Various co-factors, salts, and buffers may be included, where ionic and buffer species are typically optimized with regard to product production. When changing the concentration of a particular component of the reaction medium, that of another component may be changed accordingly. Also, the concentration levels of components in the reactor may be varied over time. The adjuster of oxidation/reduction potential may be NADPH, tris(2-carboxyethyl)phosphine (TCEP), dithiothreitol, ascorbic acid, glutathione and/or their oxidized forms.

In a semi-continuous operation mode, the reactor may be operated in dialysis, diafiltration batch or fed-batch mode. A feed solution may be supplied to the reactor through the same membrane or a separate injection unit. Synthesized product is accumulated in the reactor, and then is isolated and purified according to the usual method for purification after completion of the system operation.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump or by applying transmembrane pressure using other methods known in the art. The solution in contact with the outside surface of the membrane may be cyclically changed, and may be in a steady tangential flow with respect to the membrane. The reactor may be stirred internally or externally by proper agitation means.

The amount of product produced in a reaction can be measured in various fashions. One method relies on the availability of an assay which measures the activity of the particular product being produced.

Methods and Compositions

In some embodiments, the subject method is a method of treating a subject for sepsis or a septic condition with an effective dose of a Lipid A antagonist. In some embodiments a Lipid A antagonist is administered to prevent severe virus infection sequelae. In some embodiments a TLR4 agonist is administered as an adjuvant to enhance an immune response. In some embodiments, the subject method includes administering to the subject an effective amount of a formulation as described above. In some embodiments, the subject is human. In some embodiments, the compound is administered as a pharmaceutical preparation.

The subject compounds and methods find use in a variety of therapeutic applications. Therapeutic applications of interest include those applications in which infection or an immune response is the cause or a compounding factor in disease progression. As such, the subject compounds find use in the treatment of a variety of different conditions in which the inhibition and/or treatment of immune responsiveness in the host is desired.

The terms "active agent," "antagonist", agonist, "drug" and "pharmacologically active agent" are used herein to refer to a chemical material or compound of the invention which, when administered to an organism (human or animal) induces a desired pharmacologic and/or physiologic effect by local and/or systemic action.

As used herein, the terms "treatment," "treating," and the like, refer to obtaining a desired pharmacologic and/or physiologic effect, such as enhancing an immune response, reducing sepsis, etc. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

The terms "individual," "host," "subject," and "patient" are used interchangeably herein, and refer to an animal, including, but not limited to, human and non-human primates, including simians and humans; rodents, including rats and mice; bovines; equines; ovines; felines; canines; avians, and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated. As described above, compounds of the invention, e.g. of Formula I, including structures 6a-6e, The term "unit dosage form," as used herein, refers to physically discrete units suitable as unitary dosages for human and animal subjects, each unit containing a predetermined quantity of a compound calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

The compounds described herein can be formulated using any convenient excipients, reagents and methods. Compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the subject compound is formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some embodiments, the subject compound is formulated for sustained release.

The subject formulations can be administered orally, subcutaneously, intramuscularly, parenterally, or other route, including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ.

Each of the active agents can be provided in a unit dose of from about 0.1 µg, 0.5 µg, 1 µg, 5 µg, 10 µg, 50 µg, 100 µg, 500 µg, 1 mg, 5 mg, 10 mg, 50, mg, 100 mg, 250 mg, 500 mg, 750 mg or more. Administration may be every 4 hours, every 6 hours, every 12 hours, daily, every other day, weekly, or as empirically determined for the virus of interest and the host of interest.

The subject compounds may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

Compounds listed in Table A are predicted biosynthetic intermediates in the Lipid A pathways of known Gram-negative bacteria, and can be synthesized by appropriate substitution of one or more homologous enzymes from the target bacterium into the defined enzyme system of the present invention.

TABLE A

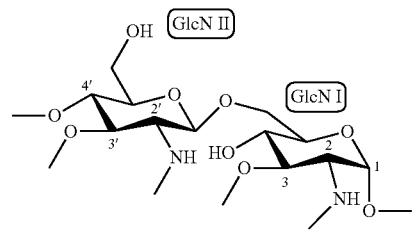

| Bacteria | GlcN II | | | GlcN I | | |
|---|---|---|---|---|---|---|
| | 4'-O | 3'-O | 2'-N | 3-O | 2-N | 1-O |
| (4 + 3)-heptaacyl glycolipids | | | | | | |
| Erwinia carotovora | P | 14:0 [3-O(12:0)] | 14:0 [3-O(12:0)] | 14:0 [3-OH] | 14:0 [3-O(16:0)] | P |
| Proteus mirabilis | P | 14:0 [3-O(14:0)] | 14:0 [3-O(14:0)] | 14:0 [3-OH] | 14:0 [3-O (16:0)] | P |
| Salmonella minnesota | P | 14:0 [3-O(14:0)] | 14:0 [3-O(12:0)] | 14:0 [3-OH] | 14:0 [3-O(16:0)] | P |
| Acinetobacter radioresistens | P | 12:0 [3-O(12:0)] | 12:0 [3-O(12:0)] | 12:0 [3-OH] | 14:0 [3-O(12:0)] | P |
| Acinetobacter baumannii | P | 12:0 [3-O(12:0)] | 14:0 [3-O((2-OH)-12:0)] | 12:0 [3-OH] | 14:0 [3-O(12:0)] | P |
| Hafnia alvei | P | 14:0 [3-O(14:0)] | 12:0 [3-O(12:0)] | 12:0 [3-OH] | 14:0 [3-O(16:0)] | P |
| Halomonas magadiensis | P | 12:0 [3-O(16:0)] | 12:0 [3-O(14:0)] | 12:0 [3-OH] | 12:0 [3-O(10:0)] | P |
| Moraxella catarrhalis | P | 12:0 | 12:0 [3-O(10:0)] | 12:0 [3-O(10:0)] | 12:0 [3-O(12:0)] | P |
| (4 + 2)-hexaacyl glycolipids | | | | | | |
| Escherichia coli | P | 14:0 [3-O(14:0)] | 14:0 [3-O(12:0)] | 14:0 [3-OH] | 14:0 [3-OH] | P |
| Campylobacter jejuni | EtNPP | 14:0 [3-O(14:0)] | 14:0 [3-O(16:0)] | 14:0 [3-OH] | 14:0 [3-OH] | EtNPP |
| Haemophilus influenzae | H | 14:0 [3-O(14:0)] | 14:0 [3-O(12:0)] | 14:0 [3-OH] | 14:0 [3-OH] | P |
| Leptospira interrogans | H | 14:0 [3-O(cis-$\Delta^5$-12:1)] | 14:0 [3-O(cis-$\Delta^5$-14:1)] | 12:0 [3-OH] | 16:0 [3-OH] | P |
| Plesiomonas shigelloides | P | 14:0 [3-O(12:0)] | 14:0 [3-O(cis-$\Delta^9$-16:1)] | 14:0 [3-OH] | 14:0 [3-OH] | P |

TABLE A-continued

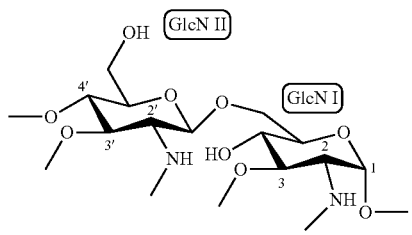

| Bacteria | GLcN II | | | GlcN I | | |
|---|---|---|---|---|---|---|
| | 4'-O | 3'-O | 2'-N | 3-O | 2-N | 1-O |
| *Salmonella typhinurium* | P | 14:0 [3-O(14:0)] | 14:0 [3-O(12:0)] | 14:0 [3-OH] | 14:0 [3-OH] | P |
| *Yersinia pestis* | P | 14:0 [3-O(12:0)] | 14:0 [3-O(cis-Δ⁹-16:1)] | 14:0 [3-OH] | 14:0 [3-OH] | P |
| *Aeromonas salmonicida* | P | 14:0 [3-O(cis-Δ⁹-16:1)] | 14:0 [3-O(12:0)] | 14:0 [3-OH] | 14:0 [3-OH] | H |
| *Bacteriovorax stolpii* | EtNPP | 14:0 [3-O(13:0)]* | 14:0 [3-O(13:0)]* | 14:0 [3-OH] OR 15:0 [3-OH]* | 14:0 [3-OH] OR 15:0 [3-OH] | P |
| *Bdellovibrio bacteriovorus* | Man | 13:0 [3-O((2-OH)-13:0)] | 13:0 [3-O((2-OH)-13:0)] | 13:0 [3-OH] | 13:0 [3,4-OH] | Man |
| *Fusobacterium nucleatum* | P | 14:0 [3-O(14:0)] | 16:0 [3-O(14:0)] | 14:0 [3-OH] | 16:0 [3-OH] | P |
| *Rhodospirillum fulvum* | Heptose | 14:0 [3-O(12:0)] | 14:0 [3-O(16:0)] | 14:0 [3-OH] | 14:0 [3-OH] | GalA |
| *Shewanella pacifica* (3 + 3)-hexaacyl glycolipids | P | 13:0 [3-O(13:0)] | 12:0 [3-O(13:0)] | 13:0 [3-OH] | 13:0 [3-OH]* | P |
| *Chromobacterium violaceum* | P | 10:0 [3-OH] | 12:0 [3-O(12:0)] | 10:0 [3-OH] | 12:0 [3-O(12:0)] | P |
| *Comamonas testeroni* | P | 10:0 [3-OH] | 10:0[3-O(12:0)] | 10:0 [3-OH] | 10:0 [3-O(14:0)] | P |
| *Neisseria meningitidis* | P | 12:0 [3-OH] | 14:0 [3-O(12:0)] | 12:0 [3-OH] | 14:0 [3-O(12:0)] | P |
| *Pseudomonas aeruginosa* | P | 10:0 [3-OH] | 12:0 [3-O(12:0)] | 10:0 [3-OH] | 12:0 [3-O(12:0)] | P |
| *Pseudomonas reactans* | P | 10:0 [3-OH] | 12:0 [3-O(12:0)] | 10:0 [3-OH] | 12:0 [3-O(12:0)] | P |
| *Xanthomonas campestris* | P | 10:0 [3-O(10:0)] | 12:0 [3-OH] | 10:0 [3-O(10:0)] | 12:0 [3-OH] | P |
| *Brucella abortus* | P | 16:0 [3-O((27-OH)-28:0)] | 14:0 [3-OH] | 14:0 [3-O(18:0)] | 12:0 [3-OH] | P |
| *Xanthomonas campestris* (3 + 2)-pentaacyl glycolipids | EtNPP | 10:0 [3-O(13:0)] | 12:0 [3-OH] | 10:0 [3-O(13:0)] | 12:0 [3-OH] | EtNPP |
| *Bacteroides fragilis* | H | 16:0 [3-OH] | 17:0 [3-O(15:0)]* | 15:0 [3-OH] | 16:0 [3-OH] | P |
| *Burkholderia cepacia complex* | Ara4N-P | 14:0 [3-OH] | 16:0 [3-O(14:0)] | 14:0 [3-OH] | 16:0 [3-OH] | P-Ara4N |
| *Burkholderia cepacia* | P | 14:0 [3-OH] | 16:0 [3-O(14:0)] | 14:0 [3-OH] | 16:0 [3-OH] | P |
| *Flavobacterium maningosepticum* | P | 16:0 [3-OH] | 17:0 [3-O(15:0)]* | 15:0 [3-OH]* | 17:0 [3-OH]* | P |
| *Leptospira interrogans* | GalA | 14:0 [3-O(18:0)] | 16:0 [3-OH] | 14:0 [3-OH] | 16:0 [3-OH] | GalA |
| *Neisseria gonorrhoeae* | P | 12:0 [3-OH] | 14:0 [3-O(12:0)] | 12:0 [3-OH] | 14:0 [3-OH] | P |
| *Bacteroides gingivalis* | H | 15:0 [3-OH]* | 17:0 [3-O(16:0)]* | 16:0 [3-OH] | 17:0 [3-OH]* | P |
| *Rhizobium etli* | GalA | 14:0 [3-OH] | 14:0 [3-O(28:0)] | 14:0 [3-OH] | 18:0 [3-OH] | H |
| *Rhodobacter sphaeroides* | P | 10:0 [3-OH] | 16:0 [3-O(cis-Δ⁷-16:1)] | 10:0 [3-OH] | 14:0 [3-OH] | P |
| *Rhodobacter capsulatus* | P | 14:0 [3-O(cis-Δ⁵-12:1)] | 16:0 [3-OH] | 1400 [3-OH] | 14:0 [3-OH] | P |
| *Sinorhizobium sp.* | P | 14:0 [3-OH] | 16:0 [3-OH] | 14:0 [3-OH] | 18:0 [3-OH] | P |
| *Agrobacterium tumefaciens* | P | 14:0 [3-OH] | 16:0 [3-O((27-O(3-OH 4:0)28:0] | 14:0 [3-OH] | 16:0 [3-OH] | P |
| *Alteromonas macleodii* | P | 14:0 [3-OH] | 12:0 [3-O(12:0)] | 12:0 [3-OH] | 12:0 [3-OH] | P |
| *Aquifex pyrophilus* | GalA | 14:0 [3-O(18:0)] | 16:0 [3-OH] | 14:0 [3-OH] | 14:0 [3-OH] | GalA |
| *Azospirillum lipoferum* | H | 14:0 [3-OH] | 16:0 [3-O(18:0)] | 14:0 [3-OH] | 16:0 [3-OH] | GalA |
| *Bartonella henseale* | P | 12:0 [3-OH] | 16:0 [3-O((27-OH)-28:0)] | 12:0 [3-OH] | 16:0 [3-OH] | P |

TABLE A-continued

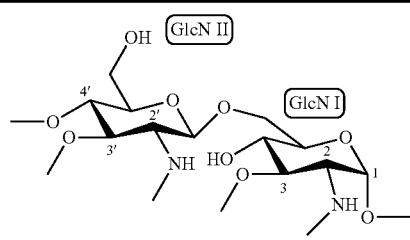

| Bacteria | GLcN II 4'-O | 3'-O | 2'-N | GlcN I 3-O | 2-N | 1-O |
|---|---|---|---|---|---|---|
| *Bordetella pertussis* | GalN-P | 14:0 [3-OH] | 14:0 [3-O(14:0)] | 10:0 [3-OH] | 14:0 [3-OH] | P-GalN |
| *Chlamydia trachomatis* | P | 14:0 OR 16:0 | 20:0 [3-O(18:0)] | 14:0 OR 15:0 | 20:0 [3-OH] | P |
| *Porphyromonas gingivalis* (2 + 3)-pentaacyl glycolipids | P | 15:0 [3-OH]* | 17:0 [3-O(16:0)]* | 10:0 [3-OH] | 17:0 [3-OH]* | P |
| *Marinomonas vaga* | H | — | 10:0 [3-O(10:0)] | 14:0 [3-OH] | 10:0 [3-O(10:0)] | P |
| *Pseudoalteromonas nigrifaciens* (2 + 2)-tetraacyl glycolipids | P | 10:0 [3-OH] | 12:0 [3-OH] | 16:0 [3-OH] | 12:0 [3-O(12:0)] | P |
| *Escherichia coli* mutant | H | 14:0 [3-OH] | 14:0 [3-OH] | 14:0 [3-OH] | 14:0 [3-OH] | P |
| *Francisella tularensis* | H | — | 18:0 [3-O(C14:0)] | 16:0 [3-OH] | 16:0 [3-OH] | H |
| *Helicobacter pylori* | H | — | 18:0 [3-O(C16:0)] | 16:0 [3-OH] | 18:0 [3-OH] | P |
| *Bordetella parapertussis* | P | 10:0 [3-OH] | 14:0 [3-O(14:0)] | 16:0 | 14:0 [3-OH] | P |
| *Coxiella burnetii* | P | 15:0 OR 16:0 | 16:0 [3-OH] | 16:0 | 16:0 [3-OH] | P |

*iso-branched fatty acyl chains
P: phosphate EtNPP: 2-aminoethylpyrophosphate
Man: D-mannose
GalA: galacturonic acid
Ara4N: 4-amino arabinose
GalN: D-galactosamine

Example 1

Defined Enzymatic Synthesis of Lipid A Analogs

Lipid A, monophosphoryl Lipid A, and Lipid $IV_A$ are structurally related glycolipids that elicit drastically different biological responses in humans. This family of molecules is found in the outer membranes of all Gram-negative bacteria, and exhibits considerable variation in the number, position, length, and degree of unsaturation of its fatty acyl substituents. Notwithstanding impressive advances in their total synthesis, the unavailability of facile methods to prepare structurally defined analogs of these natural products represents a major roadblock in our understanding of their remarkable immuno-modulatory properties. Here we present a fundamentally novel approach to access these structure-activity relationships. By Our reconstituted multienzyme system revealed considerable tolerance for orthologs with distinct substrate specificity, as illustrated by swapping enzymes from distantly related bacteria, including *Synechococcus* sp. and *Bacteroides thetaiotaomicron*. The ability to rapidly analyze the biosynthetic features of enzymes from virtually any Lipid A pathway opens the door to elucidating and exploiting the functional diversity of this singularly important family of metabolites from the human microbiota.

Our target for this study was Lipid $IV_A$, the first bioactive intermediate in the Lipid A biosynthetic pathway. Lipid $IV_A$ bears two fewer acyl chains but is otherwise identical to Lipid A (FIG. 1). In mice, it is a endotoxin-like agonist, but in humans it is an antagonist of Lipid A by virtue of its ability to bind to TLR4-MD2 without eliciting a signaling response from this transmembrane receptor. Synthetic analogs of Lipid $IV_A$ have been investigated as potential treatments of severe sepsis, whereas other analogs have the potential to be vaccine adjuvants. The fundamental building blocks for Lipid $IV_A$ biosynthesis are acetyl-CoA and UDP-N-acetylglucosamine (UDP-GlcNAc) with NAD(P)H and ATP as essential cofactors. By individually purifying 19 *E. coli* proteins and reconstituting them in vitro along with these substrates and cofactors, we have developed a chemically defined system capable of synthesizing Lipid $IV_A$ at a high rate (1 $s^{-1}$, normalized to the fatty acid synthase concentration) and stoichiometric efficiency (50% yield on an acetyl-CoA basis).

Expression and Purification of Components of Lipid $IV_A$ Biosynthesis Pathway. The biosynthetic pathway of Lipid $IV_A$ (FIG. 1) can be operationally divided into four modules. Module A, comprised of AccC, AccA, AccD, and holo-AccB (with a tethered biotin cofactor), converts acetyl-CoA into malonyl-CoA. In the presence of NADPH, acetyl-CoA and malonyl-CoA initiate synthesis of a fatty acyl chain via the collaborative activity of FabH, FabD, FabG, FabA or FabZ, FabI, and holo-ACP (which harbors a tethered phosphopantetheine arm) (Module B). Additional malonyl-CoA equivalents are consumed by FabB or FabF, FabD, FabG, FabA or FabZ, and FabI (Module C) to elongate the butyryl-ACP thioester product of module B. Whereas this pathway generates saturated or monounsaturated fatty acyl chains of varying lengths for purposes of phospholipid synthesis, a fourth module (Module D) comprised of six enzymes (LpxA, LpxC, LpxD, LpxH, LpxB, and LpxK) hijacks the 3-hydroxymyristoyl-ACP intermediate from the fatty acid synthase to yield Lipid $IV_A$.

Figure 2:
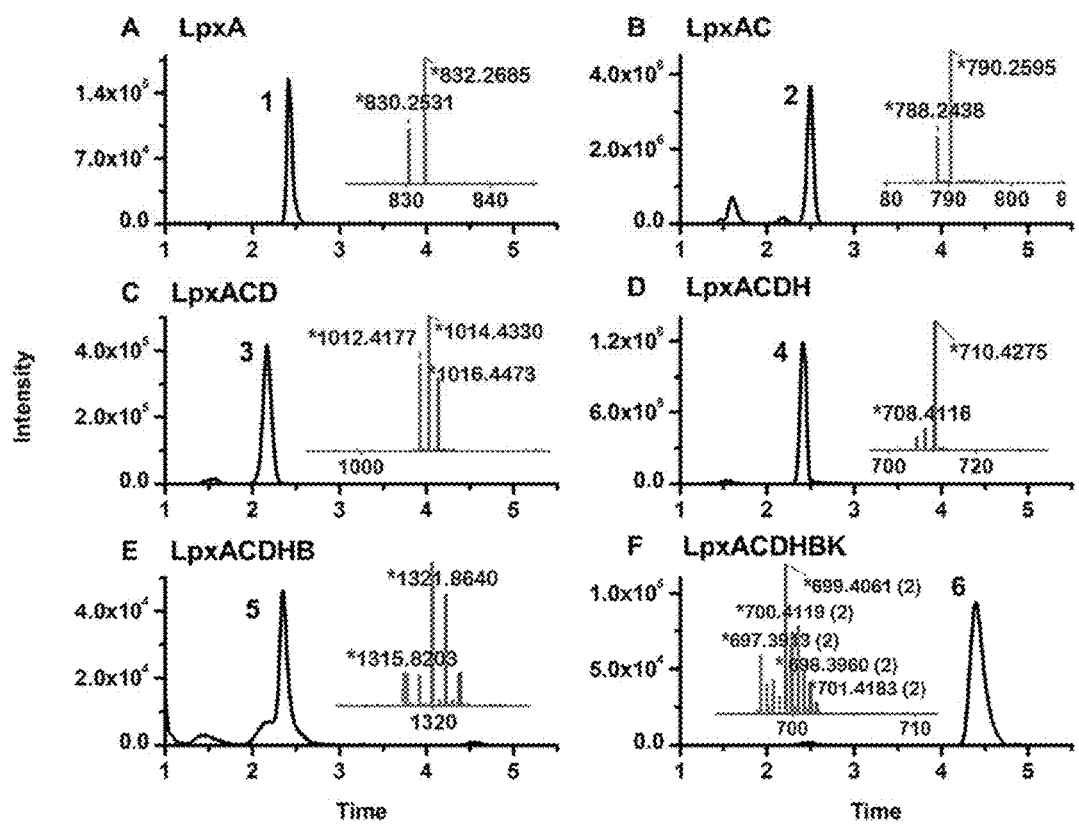
FIG. 2. Products 1-6 detected by LC-ESI MS under different assay conditions. (A) 1 was formed when Module A-C was incubated with all the cofactors together with LpxA. (B) 2 was formed when Module A-C was incubated with all the cofactors together with LpxA and LpxC. (C) 3 was formed when Module A-C was incubated with all the cofactors together with LpxA, LpxC and LpxD. (D) 4 was formed when Module A-C was incubated with all the cofactors together with LpxA, LpxC, LpxD and LpxH. (E) 5 was formed when Module A-C was incubated with all the cofactors together with LpxA, LpxC, LpxD, LpxH and LpxK. (F) 6 was formed when Module A-C was incubated with all the cofactors together with LpxA, LpxC, LpxD, LpxH, LpxK and LpxB. Insets indicate the [M-H]⁻ or (in the case of compound 6) $[M-2H]^{2-}$ ion of each lipid intermediate produced by the reconstituted system.

The *E. coli* ACC and FAS components were individually expressed and purified, as described before. See Yu et al. (2011) PNAS 108(46):18643-18648; and Xiao et al. (2013) Biochemistry 52(46):8304-8312, each herein specifically incorporated by reference. Similarly, *E. coli* LpxA, LpxC and LpxD were individually expressed and purified. Because LpxH, LpxB and LpxK are membrane-associated proteins, their expression and purification required additional procedures To ascertain activity of purified enzymatic components of Lipid A biosynthesis pathway, 5 μM each of LpxA, LpxC, LpxD, LpxH, LpxB, and LpxK were mixed with 10 μM holo-AccB, 10 μM holo-ACP, and 1 μM each of all other enzymes shown in Scheme 1. Control reactions lacking LpxK, LpxK/B, LpxK/B/H, LpxK/B/H/D, and LpxK/B/H/D/C were also performed. Reactions were initiated by the addition of a cocktail comprising of 600 μM acetyl-CoA, 1 mM ATP, 1.3 mM NADPH, 1 mM UDP-GlcNAc, 5 mM $MgCl_2$ and 15 mM buffered sodium carbonate (pH 7.2), and allowed to proceed to completion for ca. 12 h. Each reaction mixture was lyophilized and resuspended in methanol prior to mass spectrometric analysis. As seen in FIG. 1, high-resolution LC-ESI-MS$^n$ analysis on a SCIEX TripleTOF system verified formation of the expected products, including Lipid $IV_A$, in each reaction mixture that contained the appropriate protein components (FIG. 2).

In vitro System Turnover Rate and Stoichiometric Synthesis of Lipid $IV_A$. In earlier experiments utilizing an endogenous thioesterase (TesA from *E. coli*) as a release mechanism, we established conditions under which Modules A-C collectively turned over at a high rate (>10 min$^{-1}$) and with stoichiometric yield (on an acetyl-CoA as well as NADPH basis), Xiao et al., supra. Under steady-state conditions, Modules A-C supplemented with TesA predominantly synthesized a mixture of saturated and cis-(ω-7) monounsaturated $C_{14}$-$C_{18}$ fatty acids. Accordingly, our efforts to reconstitute Lipid $IV_A$ biosynthesis were initiated by replacing TesA with equimolar ratios of the six enzymes of the Lipid A pathway, LpxA, LpxC, LpxD, LpxH, LpxB and LpxK. We anticipated that 3-hydroxymyristoyl-ACP would be hijacked by LpxA and LpxD at some frequency. However, two questions arose. First, to what extent would longer chain (i.e., $C_{16}$ and $C_{18}$) acyl-ACP intermediates be dead-end inhibitors of the system? And second, what would be the fate of monounsaturated intermediates beyond cis-3-decenoyl-ACP, given that *E. coli* Lipid A is generally regarded as being exclusively derived from saturated fatty acyl chains.

Figure 3:
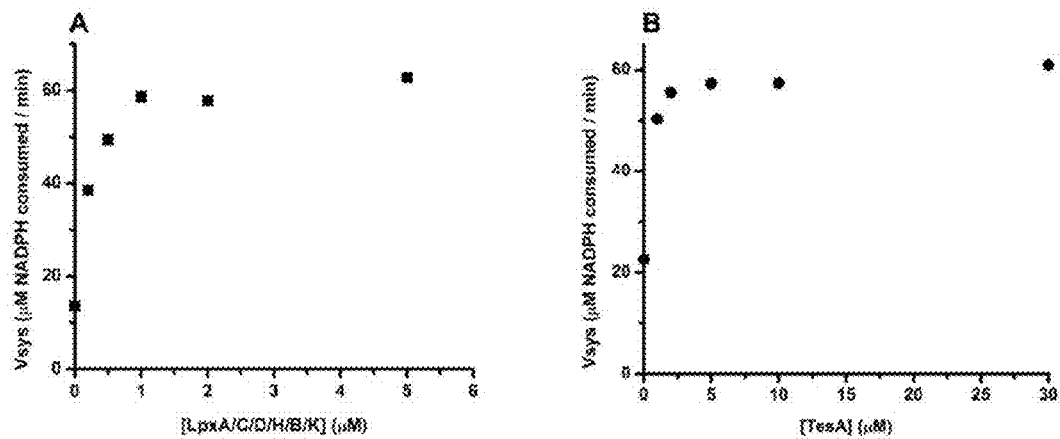
FIG. 3. Titration of an equimolar ratio of (A) LpxA:LpxC:LpxD:LpxH:LpxB:LpxK; and (B) the TesA thioesterase into an enzymatic mixture harboring the proteins from Modules A-C(Scheme 1). In each case, the assay mixture included 10 μM holo-ACP, 10 μM holo-AccB, and 1 μM of all other protein components from Modules A-C. Substrate and cofactor concentrations were as follows: 600 μM acetyl-CoA, 1 mM ATP, 1.3 mM NADPH, 1 mM UDP-GlcNAc, 5 mM $MgCl_2$ and 15 mM $NaHCO_3$.

Next, we sought to evaluate the proficiency of the acyl transferases for hijacking the 3-hydroxymyrystoyl-ACP intermediate from the fatty acid synthase. An equimolar ratio of LpxA:LpxC:LpxD:LpxH:LpxB:LpxK was titrated into a system comprised of 1 μM each of all enzymatic components of Modules A-C and 10 μM each of holo-AccB and holo-ACP. Three properties were simultaneously measured—the overall turnover rate, accumulation of Lipid $IV_A$ as a function of time, and accumulation of "dead-end" acyl-ACPs as a function of time. The steady state turnover rate of this multi-enzyme pathway attained saturation when the Lipid A biosynthetic enzymes were present in modest excess over the acetyl-CoA carboxylase and fatty acid synthase enzymes (FIG. 3A). Moreover, the turnover rate under saturation conditions was comparable to that achieved in the presence of saturating concentrations of TesA, an acyl-ACP thioesterase (FIG. 3B). Together, these findings suggest that, at reasonable relative concentrations, LpxA and LpxD are able to efficiently divert carbon flux from fatty acid metabolism into the Lipid A pathway.

Figure 4:
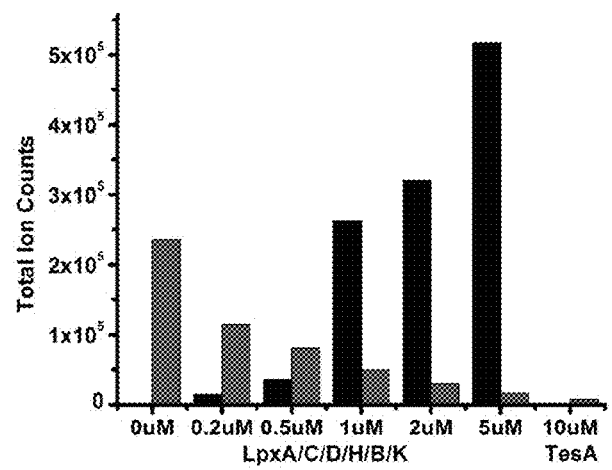
FIG. 4. Quantification of Lipid $IV_A$ and its analogs as well as long-chain ("dead-end") acyl-ACP species. Lipid $IV_A$ (m/z 701.4197) and unsaturated analogs (m/z 700.4119, 699.4041, 698.3962 and 697.3884) were quantified by LC-ESI-MS with a width of ±0.01 a.m.u (black bars).

To verify and extend this conclusion, both the product composition and the accumulated acyl-ACP intermediates were analyzed under conditions corresponding to ca. 10 turnovers of the fatty acid synthase. Lipid $IV_A$ analogs were analyzed by mass spectrometry, as outlined above. Acyl-ACP intermediates were identified in a data-independent SWATH acquisition mode in which the first quadrupole was stepped through increments of 3 a.m.u. across the m/z range spanning the holo-ACP and arachidyl-ACP. The ACP ions from each 3 a.m.u. window were fragmented in the collision cell, resulting in release of phophopantetheinyl (Ppant) ions. The predominant ions observed via this PPant ejection assay corresponded to stearyl-ACP (C18:0), arachidyl-ACP (C20:0), oleyl-ACP (C18:1), and gondoyl-ACP (C20:1). Quantification of these long chain acyl-ACPs was achieved by comparing the ratios of the intact protein and the Ppant ion pairs (Fig. S7-9). As shown in FIG. 4, the yield of Lipid $IV_A$ analogs increased with increasing concentrations of the Lpx enzymes, along with a concomitant reduction in long chain acyl-ACP products. Notably when Lpx enzymes were used in five-fold excess, the abundance of these "dead-end" products was comparable to that observed in a control assay containing saturating amounts of the TesA thioesterase. Together, these results highlight the catalytic efficiency of our reconstituted system for the enzymatic synthesis of bioactive Lipid A precursors.

Figure 5:
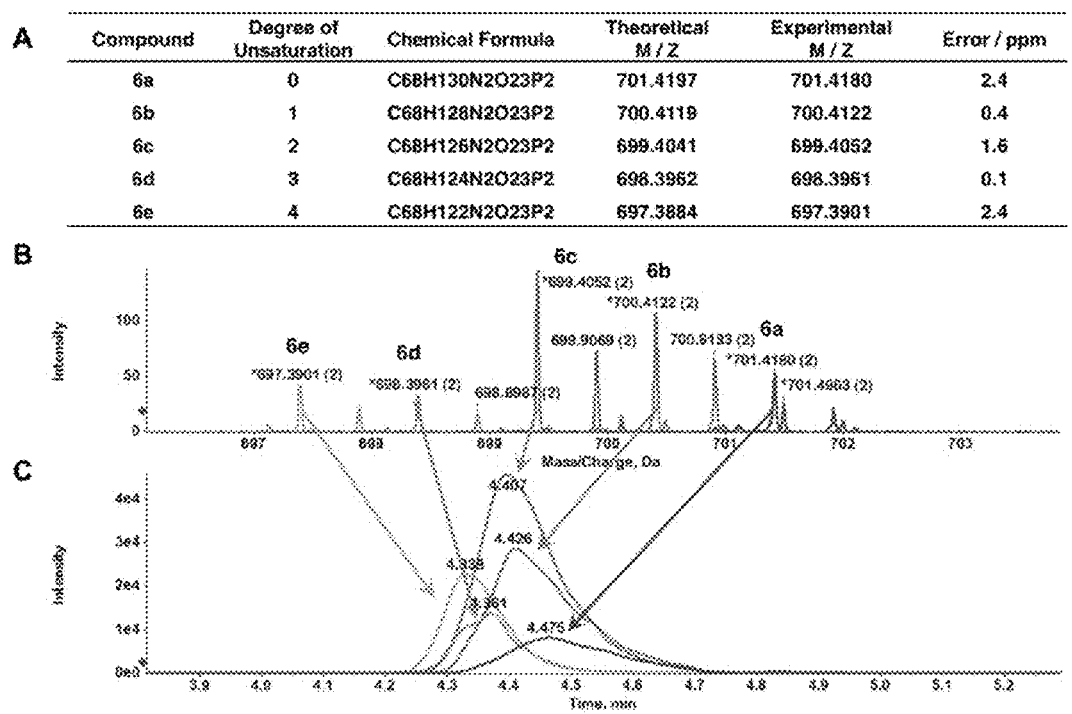
FIG. 5. Mass spectrometry analysis of Lipid $IV_A$ (6a) and analogs of with varying degrees of saturation (6b-6e). Experimental m/z values were derived from LC-QTOF analysis on a SCIEX 6600 instrument. (A) Table of m/z values of unsaturated Lipid $IV_A$ compound (6a-6e). (B) Mass spectrum and (C) extracted ion chromatograms (EIC) of unsaturated Lipid $IV_A$ compound (6a-6e).

Broad Substrate Specificity of *E. coli* Lipid A Biosynthesis Pathway. In addition to long chain acyl-ACP intermediates, the *E. coli* fatty acid synthase also produces cis-(ω-7) unsaturated fatty acyl-ACP species. Because Lipid A in this Gram-negative bacterium is exclusively derived from saturated fatty acids, and because under our assay conditions the *E. coli* fatty acid synthase is known to produce significant quantities of mono-unsaturated fatty acids, we thought that these intermediates would likely inhibit our reconstituted system. Remarkably, analogs of Lipid $IV_A$ with one or more mono-unsaturated $C_{14}$ fatty acyl chains were observed in comparable amounts to the known fully saturated natural products (FIG. 5A-C). Indeed, the most prominent products of our 19-component reconstituted system appeared to be Lipid $IV_A$ analogs with one and two degrees of unsaturation. Fragment analysis of each observed product provided additional evidence for the proposed structures (FIG. 10-14). In particular, the positions of $\Delta^7$-3-hydroxmyristoyl chains on the disaccharide could be deduced based on the assumption that ester bonds are more susceptible to fragmentation than amide bonds.

In previous studies with reconstituted fatty acid synthases, we noted that the fraction of mono-unsaturated fatty acids could be increased without kinetic penalty by increasing the relative abundance of FabB (one of two ketosynthases responsible for chain growth). Conversely, by replacing FabZ (fatty acyl-ACP dehydratase) with an ortholog from a bacterium such as *Synechococcus*, saturated fatty acids could be exclusively synthesized. Consistent with these observations, increasing the FabB concentration in the present reconstituted system tilted product balance toward unsaturated Lipid $IV_A$ analogs (Table 1). In contrast, fully saturated Lipid $IV_A$ was the most abundant product when *E. coli* FabZ was replaced with its *Synechococcus* ortholog (with concomitant elimination of FabA, which was no longer required to maintain a high turnover rate). A similar, but less pronounced, effect was also observed by increasing the concentration of *E. coli* FabZ. Together these studies suggest that *E. coli* LpxA and LpxD have considerably broader tolerance for mono-unsaturated acyl chains than previously assumed.

The broad specificity of our reconstituted Lipid IV$_A$ system for unsaturated acyl chains prompted us to revisit the structure of biosynthetic Lipid A. *E. coli* DH5α was grown under standard conditions (37C), and Lipid A was extracted using an established protocol. Consistent with earlier reports, only the fully saturated natural product was observed, suggesting that *E. coli* harbors a regulatory mechanism to suppress the incorporation of mono-unsaturated acyl chain substrates by LpxA and LpxD. We speculate that nature achieves product homogeneity by co-regulating the expression of FabZ with the early enzymes in the Lipid A pathway. In this context, it is notable that the genes encoding FabZ, LpxA, LpxC and LpxD exist as operons in many bacteria, and are not tightly linked to other fatty acid biosynthetic genes.

Antagonistic Effect of Unsaturated Lipid IV$_A$. To examine the antagonistic effect of the Lipid IV$_A$ analogues produced by our reconstituted system, products from sample 1-3 were assayed against LPS stimulated HUVEC microphage cell line. IL-6 level was measured as an indicator of TLR4 suppression. As a negative control, an in vitro reaction lacking acetyl-CoA was run and processed in parallel. Lipid IV$_A$ samples was quantified via mass spectrometry by comparing with a standard curve generated from synthetic Lipid IV$_A$ standard. In all experiment, Lipid IV$_A$ analogues and the synthetic standard were dosed at 100 and 500 ng/mL for an hour prior to addition of 100 ng/mL LPS.

Figure 6:
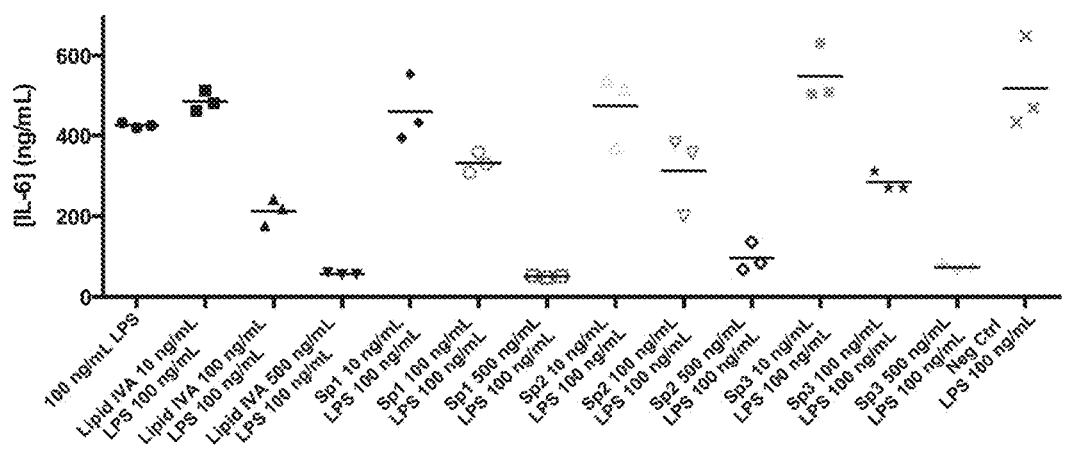
FIG. 6. Antagonistic effect of unsaturated Lipid $IV_A$ analogues produced by in vitro system measured by IL-6 expression levels of HUVEC cell line treated with both Lipid $IV_A$, analogs and LPS.

The Lipid IV$_A$ analogues exhibited a similar inhibitory behavior as the synthetic standard. At 100 ng/mL, the level of IL-6 release was suppressed to approximately 50%, whereas 500 ng/mL of Lipid IV$_A$ analogues knocked down the IL-6 signal to baseline level (FIG. 6. and Table S9). Prior synthetic effort had denoted the changes in antagonistic effect of tetra-acylated Lipid IV$_A$ analogues with regard to chain length. Our observation, herein, amounted previous structure-activity relationship studies suggested the antagonistic effect of Lipid IV$_A$ to hTLR4 remained unchanged with addition of unsaturation degrees on the acyl chains.

Expression and Purification of *Bacteroides thetaiotaomicron* FabH, LpxA and LpxD. The microbial community of the human gut comprises hundreds, perhaps thousands, of bacterial species, a sizeable fraction of which consists of Gram-negative bacteria. Not only is the Lipid A biosynthetic pathway universally conserved in Gram-negative organisms, but its metabolic products are arguably the most significant modulators of gut health. Most Enterobacteriaceae, such as *Shigella* and *Klebsiella*, bear the same Lipid A structure as the representative species *Escherichia coli*. However, one of the four most dominant phyla in human gut, Bacteroidetes, has been shown to have a distinct Lipid A structure that two of the primary acyl moieties attached to the disaccharide backbone are branched fatty acyl chains. Given the challenges associated with culturing gut-derived bacteria, our reconstituted enzyme platform provides a unique way to decode the structures and functions of these bioactive metabolites. We replaced the three most significant determinants of structural diversity in our reconstituted system (FabH, LpxA and LpxD) with homologs from *Bacteroides thetaiotaomicron*, a representative Gram-negative bacteria strain in the human gut.

Figure 11:
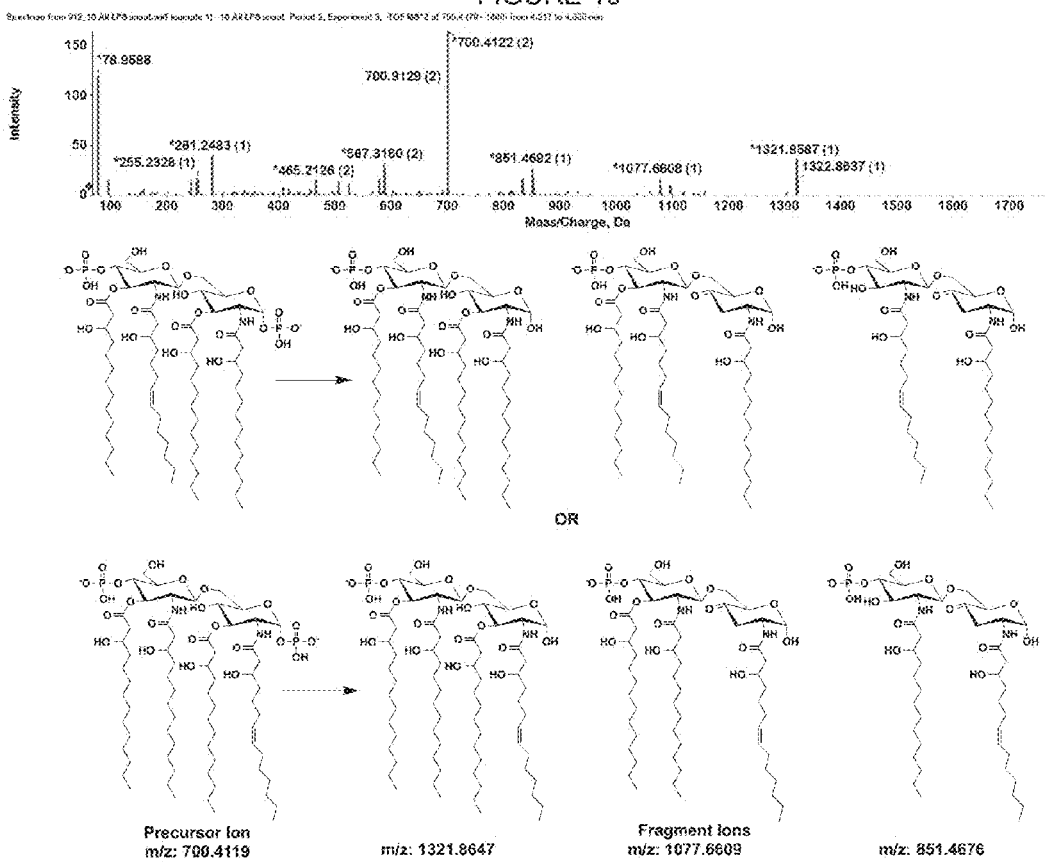
FIG. 11: Negative ion mode ESI $MS^2$ spectrum of m/z 700.4122 corresponding to alternative mono-unsaturated lipid $IV_A$ analogs derived from the in vitro reaction mixture. Structures are proposed for the observed fragment ions with m/z values of 1321.8587, 1077.6608 and 851.4692.
Figure 12:
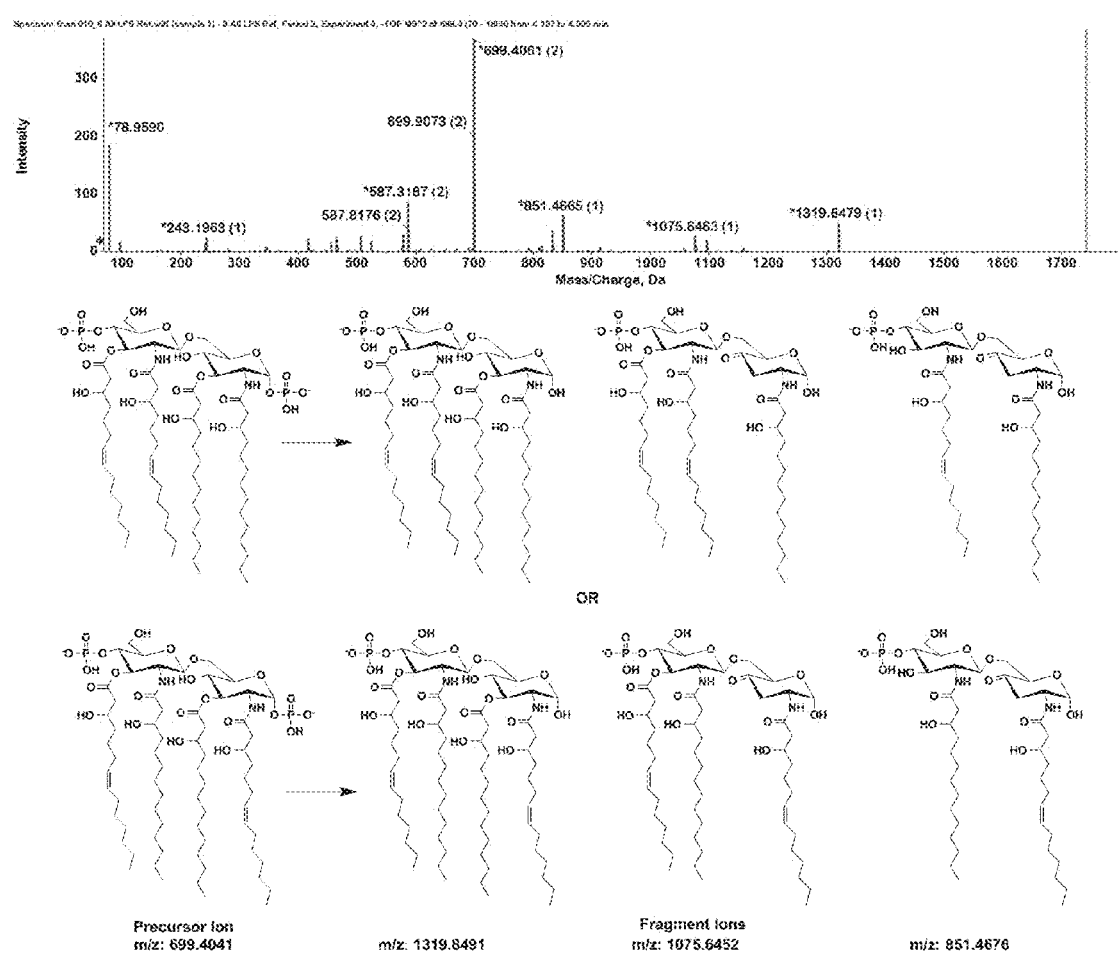
FIG. 12: Negative ion mode ESI $MS^2$ spectrum of m/z 699.4061 corresponding to alternative lipid $IV_A$ analogs harboring two mono-unsaturated chains derived from the in vitro reaction mixture. Structures are proposed for the observed fragment ions with m/z values of 1319.8479, 1075.6463 and 851.4665.
Figure 13:
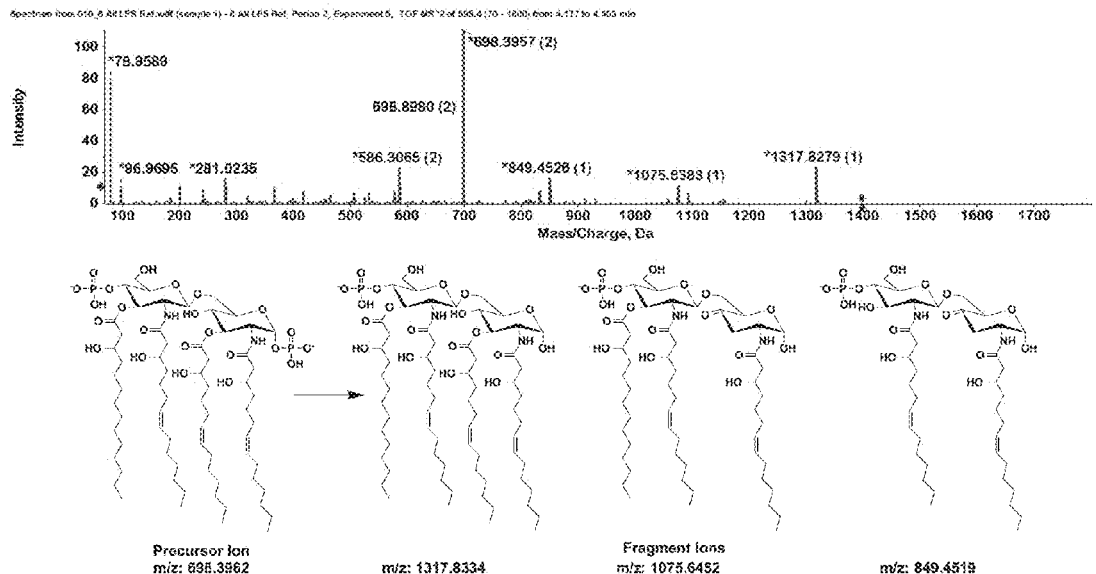
FIG. 13: Negative ion mode ESI $MS^2$ spectrum of m/z 698.395 corresponding to a lipid $IV_A$ analog harboring three mono-unsaturated chains derived from the in vitro reaction mixture. Structures are proposed for the observed fragment ions with m/z values of 1317.8279, 1075.6383 and 849.4526.
Figure 14:
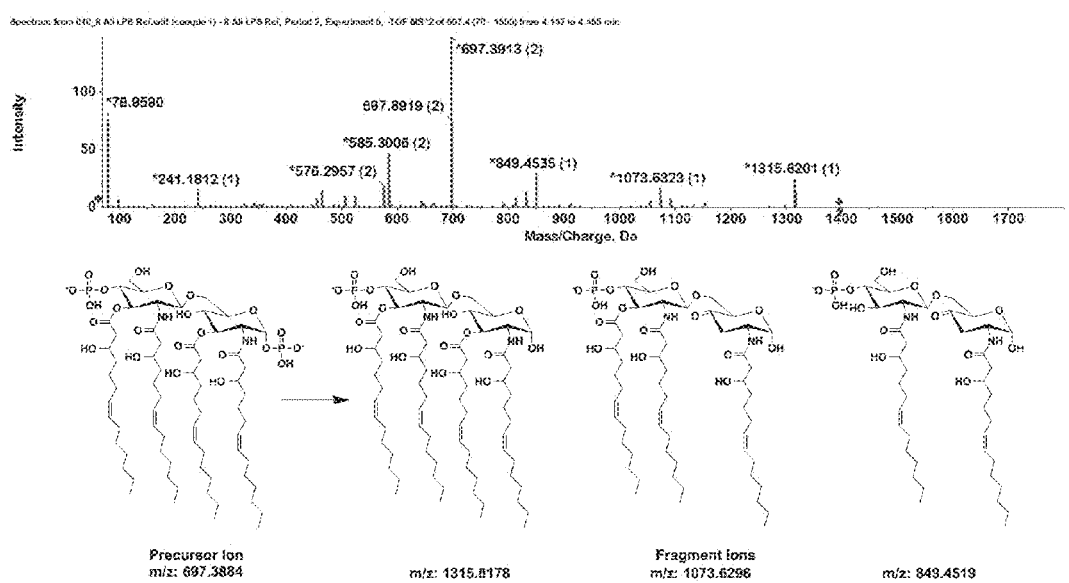
FIG. 14: Negative ion mode ESI $MS^2$ spectrum of m/z 698.395 corresponding to a lipid $IV_A$ analog harboring four mono-unsaturated chains derived from the in vitro reaction mixture. Structures are proposed for the observed fragment ions with m/z values of 1315.8201.
Figure 15:
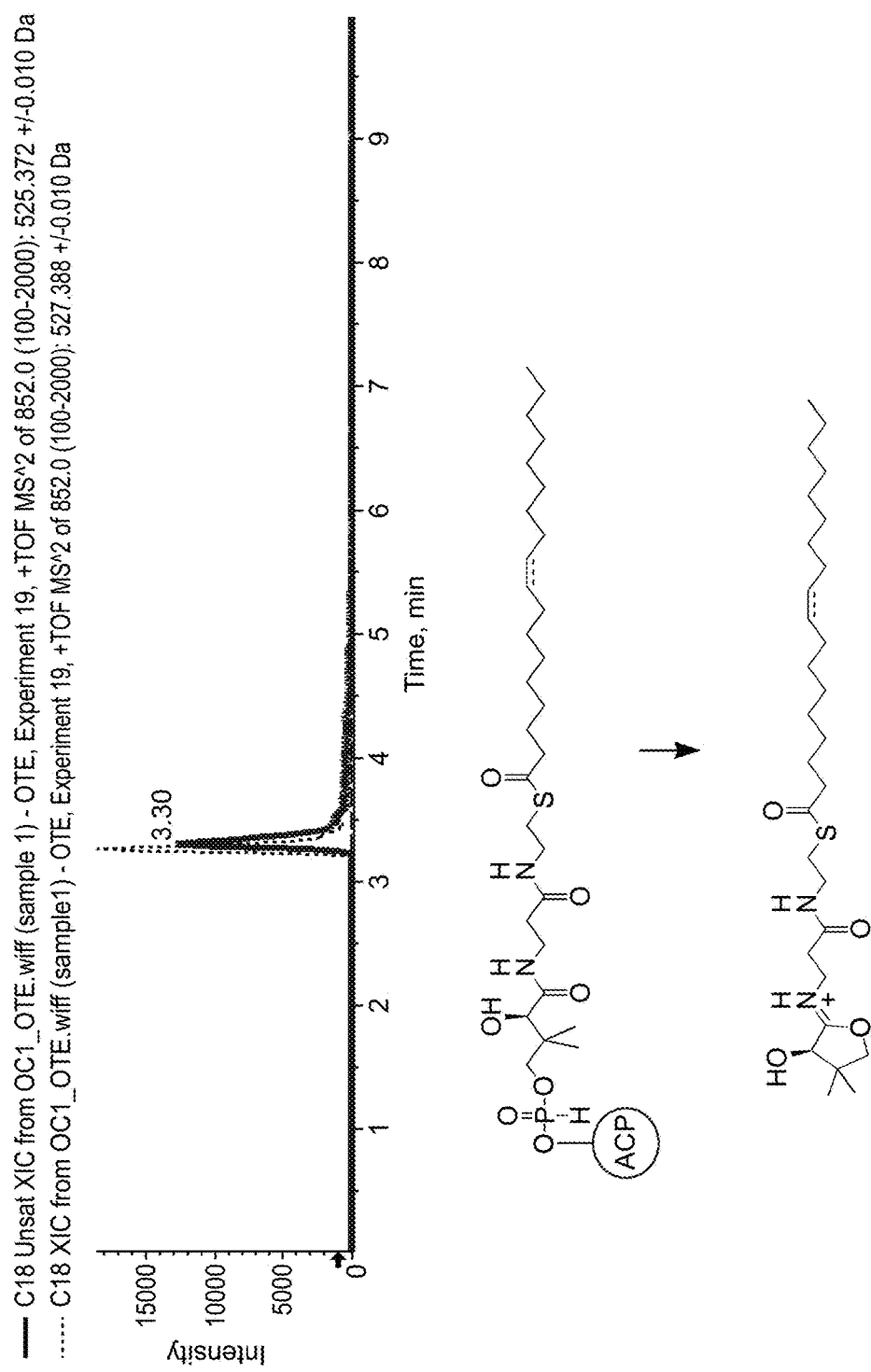
FIG. 15: Example of extracted chromatogram of stearyl-ACP ($C_{18:0}$, solid) and oleyl-ACP ($C_{18:1}$, dashed) from in vitro system containing only Module A-C.
Figure 16:
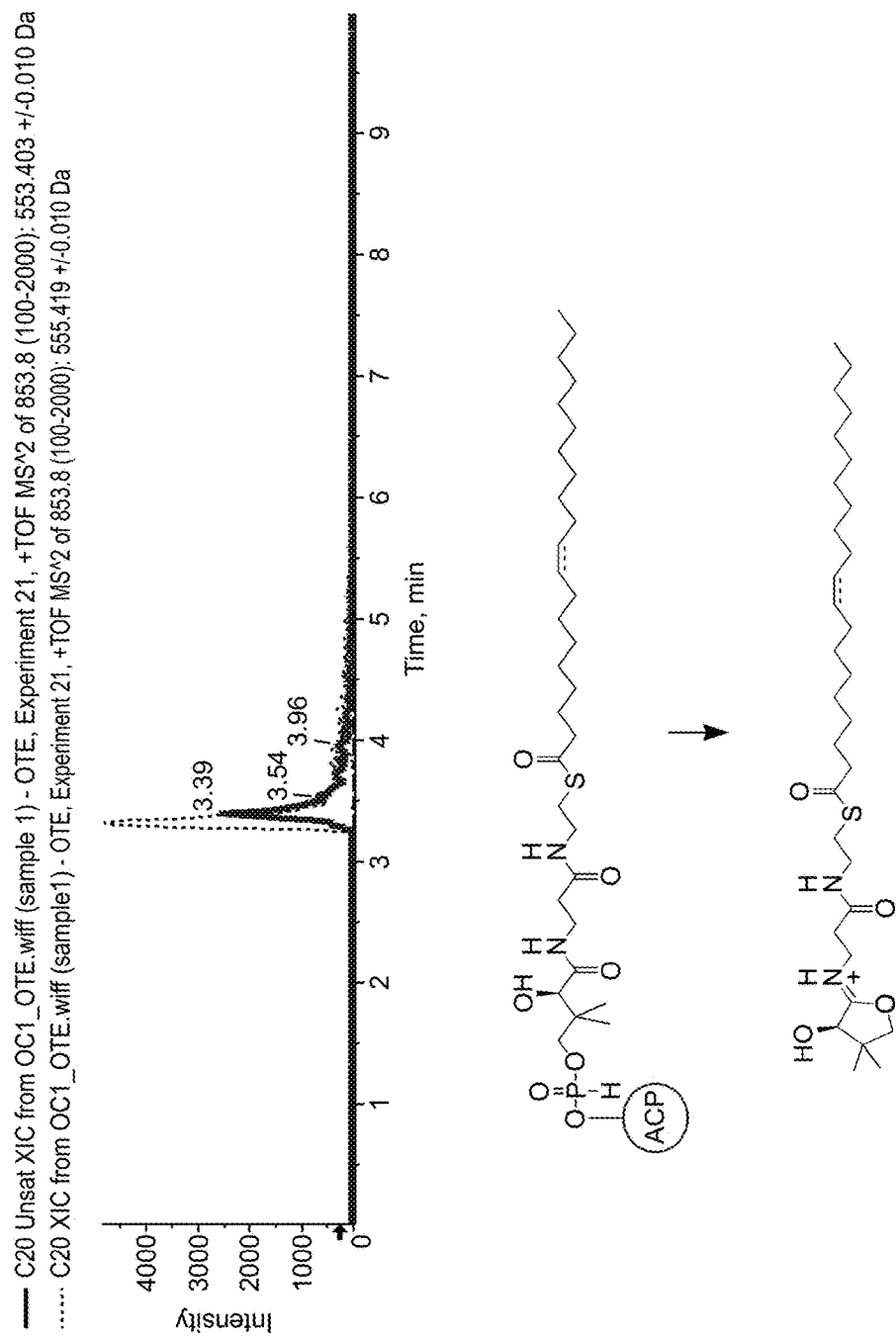
FIG. 16: Example of extracted chromatogram of arachidyl-ACP ($C_{20:0}$, solid) and gondoyl-ACP ($C_{20:1}$, dashed) from in vitro system containing only Module A-C.
Figure 17:
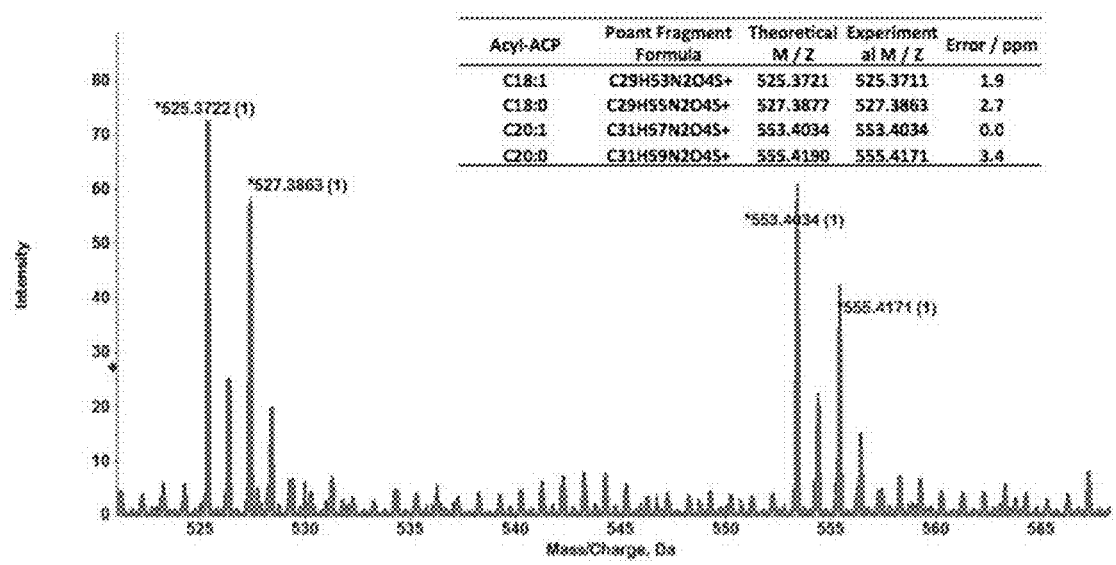
FIG. 17: TOF $MS^2$ mass spectrum of the PPant ejection product from long chain acyl-ACPs with the observed mass of ejection product (see inset).
Figure 18:
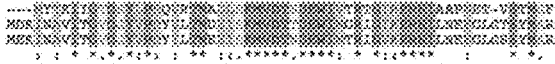
FIG. 18: Multiple sequence alignment of E. coli FabH, B. theta $FabH_1$ and $FabH_2$. Red highlights indicate the active sites and grey highlights suggest the similarity of corresponding amino acids.

BLAST search (FIG. 18) suggested that *Bacteroides thetaiotaomicron* has two 3-oxoacyl-ACp synthase homologues. The first homologue, annotated as Bt FabH$_1$, was encoded by an open reading frame consisting of 1008 bp, and shared 36% identity to Ec FabH. The second homologue, annotated as Bt FabH$_2$, was encoded by an open reading frame consisting of 1008 bp, and shared 37% identity to Ec FabH. The two homologues shared a 79% identity to each other. The two open reading frames were amplified via PCR and cloned into pET28-a vector, and the N-terminal His-tagged proteins were expressed and purified (FIG. 11).

Besides the keto-synthases, the two acyl-transferases in *B. theta* Lipid A biosynthesis pathway, Bt LpxA and Bt LpxD, necessitate the biosynthesis of Lipid A molecules with branched chain fatty acyl moieties. Hence, the genes encode Bt LpxA and Bt LpxD were amplified and cloned into a pET28-a vector, and the N-terminal His-tagged proteins were expressed and purified (FIG. 11).

Figure 7:
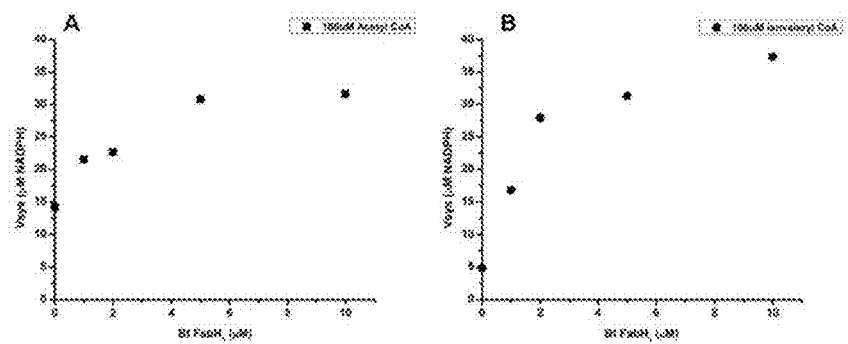
FIG. 7. Spectroscopy analyses of turnover rates of reconstituted system consisting varying concentration of Bt $FabH_1$, 1 uM Ec FabD, FabB, FabF, FabG, FabA, FabZ, FabI each, and 10 uM TesA, 1 mM TCEP, 600 uM malonyl-CoA, 1300 uM NADPH and (A) 100 uM acetyl-CoA, or, (B) 100 uM isovaleryl-CoA.

Kinetic Analysis of *B. theta* FabH Homologues. Based on the proposed structure of *B. theta* Lipid A, we hypothesized the substrates that initiate the biosynthesis of palmitic (C$_{16}$) and iso-heptadecanoic (C$_{17}$) fatty acyl moieties are acetyl-CoA and isovaleryl-CoA, respectively. To validate our hypothesis and test activities of the purified Bt FabH homologues, individual protein was titrated into *E. coli* fatty acid synthase in which either acetyl-CoA or isovaleryl-CoA was supplied as the corresponding substrate. The endogenous thioesterase TesA was also added as the release mechanism to allow the system to turn over. The turnover rate of the reconstituted system was measured by the consumption rate of NADPH via UV-vis spectroscopy (FIG. 7).

Previous studies have suggested Ec FabH is highly specific towards short chain acyl-CoA and saturates the reconstituted system at the concentration of 1 μM. In comparison, Bt FabH$_1$ demonstrated broader substrate specificity that it readily accepts both acetyl-CoA and isovaleryl-CoA. The catalytic activity of Bt FabH$_1$, however, is lower than the Ec FabH that the reconstituted system requires a concentration of 10 μM to saturate the turnover rate. Bt FabH$_2$ demonstrated low activities towards both CoA substrates. The inactivity could be due to that this homologue is a temperature sensitive protein or it is specific towards the anteiso precursors. For the purpose of this study, only Bt FabH$_1$ was used in further experiments.

Figure 8:
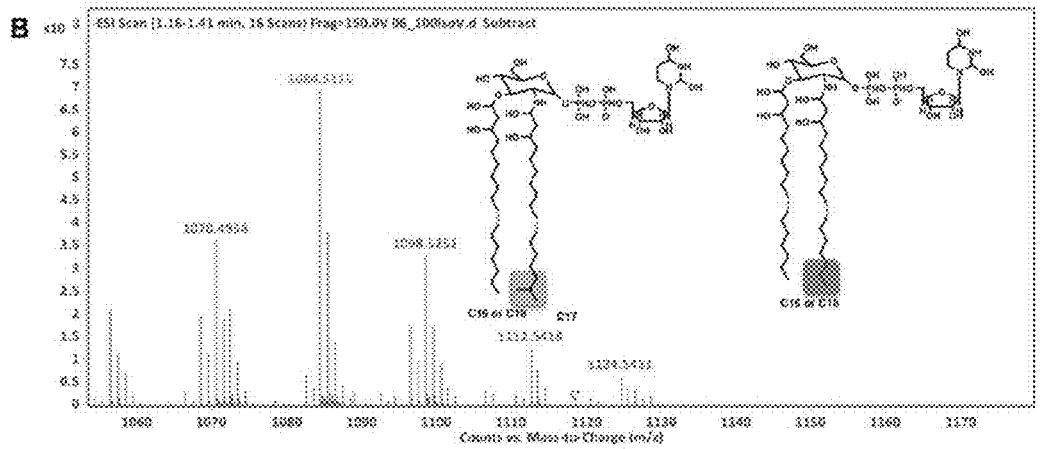
FIG. 8. Mass spectrometry analysis of straight chain and branched chain UDP-2,3-diacylglucosamine products with varying degrees of unsaturation. Experimental m/z values were derived from LC-QTOF analysis on an Agilent 6520 instrument. (A) Table of m/z values and (B) mass spectrum and of UDP-2,3-diacylglucosamine products.
Figure 9:
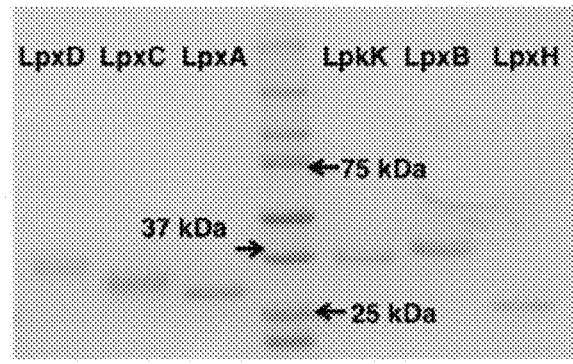
FIG. 9: SDS/PAGE analysis of purified enzymes is Lipid A biosynthesis pathway. SDS/PAGE (4~20% Tris-HCl) resolution of the proteins is shown.
Figure 10:
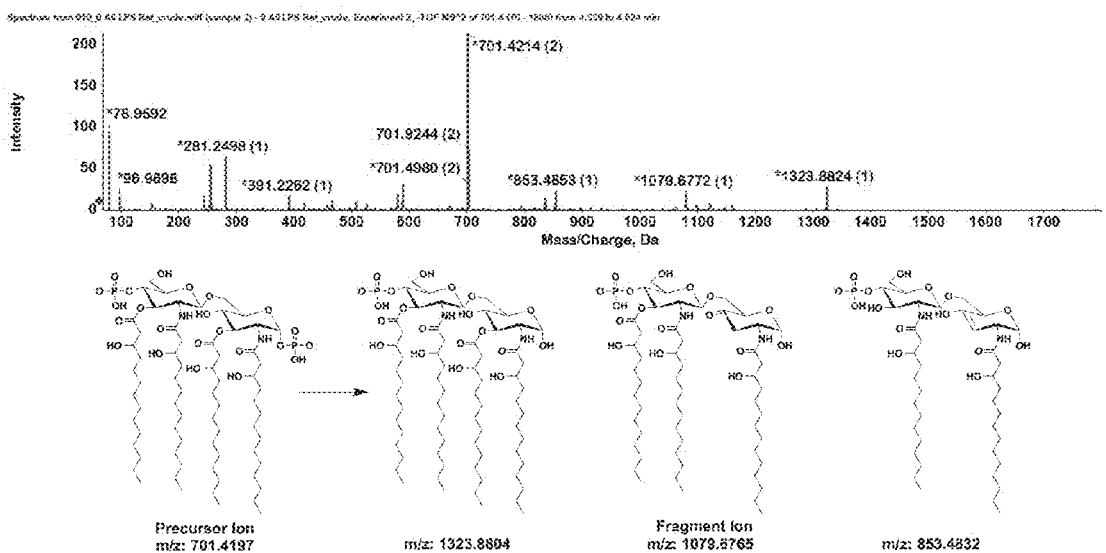
FIG. 10: Negative ion mode ESI $MS^2$ spectrum of m/z 701.4214 corresponding to (fully saturated) lipid $IV_A$ produced by the in vitro reaction mixture. Structures are proposed for the observed fragment ions with m/z values of 1323.8804, 1079.6772 and 853.4853.

Incorporation of branched chain fatty acyl moieties in UDP-2,3-diacylglcosamine intermediates. As an initial test to visualize the incorporation of straight and branched chain fatty acyl moieties into Lipid A molecules, 10 uM Bt FabH$_1$ was added into an in vitro reaction mixture containing fatty acid synthase and the first enzymes in lipid A biosynthesis pathway, Bt LpxA, Ec LpxC and Bt LpxD. We supplied the reconstituted system with three different sets of substrates. A variety of UDP-2,3-diacylglucosamine product molecules were observed via mass spectrometry (FIG. 8).

In the first set of experiment, 100 μM acetyl-CoA was added as substrate to initiate fatty acid biosynthesis. Accordingly, we observed installation of C16:0, C16:1, C18:0, C18:1 fatty acyl chains on the UDP-2,3-diacylglucasamine product. When 50 μM isovaleryl-CoA was supplied in addition to acetyl-CoA, we observed two additional product peaks, with m/z values of 1084.5 and 1112.5, which indicated the incorporation of C17:0, C17:1 or C19:0, C19:1 fatty acyl chains. When the concentration of isovaleryl-CoA was increased to 100 μM, the relative abundance of branched chain UDP-2,3-diacylglucasamine product became predominant (FIG. 19). This result demonstrated that the in vitro system is amenable towards substituting homologous catalytic component, and demonstrated the broad substrate specificities of *B. theta* Lpx A and LpxD.

In conclusion, by reconstituting 19 proteins from the *E. coli* proteome, we have established an in vitro system capable of efficient in vitro synthesis of Lipid IV$_A$, the first bioactive intermediate in the Lipid A pathway, from acetyl-CoA and UDP-GlcNAc. Although formation of Lipid A requires several additional modifications, the most important of these is the addition of the fifth and sixth fatty acyl chains. Whereas the *E. coli* enzymes that add these chains have obligate specificity for a precursor harboring the 2-keto-3- deoxy-D-mannooctanoate disaccharide unit, this sequence of events is not strictly conserved in other bacteria such as *Pseudomonas aeruginosa*. We also demonstrated that by substituting catalytic components in the system, a variety of structurally defined Lipid $IV_A$ analogues can be produced. Therefore, by mixing and matching late-stage acyltransferases from different organisms, a broader range of Lipid A analogs can be synthesized biochemically in vitro. Our unexpected discovery that the $\Delta^7$-3-hydroxymyristoyl chain can be efficiently incorporated into such compounds further enhances these possibilities.

TABLE 1

Distribution of Lipid $IV_A$ and its unsaturated analog
Percentage of Lipid $IV_A$ Analogs

| Sample | Reaction Conditions (uM) | | | Compound | | | | |
|---|---|---|---|---|---|---|---|---|
| | FabA | FabZ | FabB | 6a | 6b | 6c | 6d | 6e |
| Sp1 | 1 | 1 | 1 | 6.7% | 18.4% | 30.9% | 18.1% | 26.0% |
| Sp2 | 1 | 0 | 10 | 3.6% | 7.3% | 16.8% | 22.5% | 49.8% |
| Sp3 | 1 | 0.5 (S. FabZ) | 1 | 98.7% | 1.2% | trace | trace | trace |
| N/A | 1 | 10 | 1 | 74.3% | 19.2% | 4.2% | 1.4% | 1.2% |

Plasmid construction. Genomic DNA was isolated from *Escherichia coli* BL21 (DE3) using the DNeasy Blood and Tissue Kit (Qiagen) according to the manufacturer's instructions. Genes encoding LpxA, LpxC and LpxD were individually amplified by PCR from this genomic DNA (Table 2) and inserted into pET28a(+) (Novagen), yielding plasmids pXX24, pXX27 and pXX26, respectively. Genes encoding LpxH, LpxB and LpxK were also individually amplified and inserted into pJF89 to generate pXX32, pXX33 and pXX34, respectively. Restriction sites used for cloning these fragments are underlined. Restriction enzymes were from New England Biolabs, and T4 DNA ligase was from Invitrogen. *E. coli* DH5a was used as the cloning host.

TABLE 2

Primers for PCR

| Gene | Forward Primer | Reverse Primer |
|---|---|---|
| Ec lpxA | ATATATCATATGATTGATAAATCCGCCTTTGT (SEQ ID NO: 1) | ATATATGAATTCATGGGCTACTAGTTAACGAATCAGACCGCG (SEQ ID NO: 2) |
| Ec lpxC | ATATATCATATGATCAAACAAGGACACTTAAAC (SEQ ID NO: 3) | ATATAT CTCGAG TGCCAGTACAGCTGAAG (SEQ ID NO: 4) |
| Ec lpxD | ATATATGCTAGCATGCCTTCAATTCGACTG (SEQ ID NO: 5) | ATATATGAATTCATGGGCTACTAGTTAGTCTTGTTGATTAACCTTG (SEQ ID NO: 6) |
| Ec lpxH | ATATATCATATGGCGACACTCTTTATTGCAGA (SEQ ID NO: 7) | ATATATCTCGAGAAACGGAAAATGAATCA (SEQ ID NO: 8) |
| Ec lpxB | ATATAT CATATG ACTGAACAGCGTCCATTAAC (SEQ ID NO: 9) | ATATATCTCGAGTTGTGCTAACTCCAGAA (SEQ ID NO: 10) |
| Ec lpxK | ATATATCATATGATCGAAAAATCTGGTCTGG (SEQ ID NO: 11) | ATATATCTCGAGGTTGCCAGAAGCCAGCA (SEQ ID NO: 12) |
| Bt fabH$_1$ | ATATATCATATGGATAAAATAAATGCGGTAAT (SEQ ID NO: 13) | ATATATCTCGAG CGCATCTTCTTTGG (SEQ ID NO: 14) |
| Bt fabH$_2$ | ATATATGCTAGCATGGAAAAAATAAATGCAGT (SEQ ID NO: 15) | ATATATGAATTCATGGGCTACTAGTTACGATTCCTTTTTT (SEQ ID NO: 16) |
| Bt lpxA | ATATATCATATGGTAAGTCCTCTAGCGTATAT (SEQ ID NO: 17) | ATATATGAATTCATGGGCTACTAGTTATTTAATAATACCA (SEQ ID NO: 18) |
| Bt lpxD | ATATATCATATGGAGTTCTCGGCTAAGCAAAT (SEQ ID NO: 19) | ATATATGAATTCATGGGCTACTAGTTACTTATTTAATAGT (SEQ ID NO: 20) |

Protein Purification. Ec LpxA, EcLpxC, EcLpxD, Bt FabH$_1$, Bt FabH$_2$, Bt LpxA and Bt LpxD were expressed as cytosolic proteins in *E. coli* BL21(DE3). Transformed cells were growing at 37° C. in LB media until the OD$_{600}$ reached 0.4. Cells were then cooled to 18° C., and protein expression was induced with 0.1 mM IPTG (at OD$_{600}$~0.6). After overnight cultivation, cells were harvested by centrifugation and washed in PBS. All subsequent steps were performed at 4° C. unless indicated otherwise. Cells were resuspended in lysis buffer (50 mM Tris-HCl, 2 mM DTT, 10 mM imidazole and 150 mM NaCl, pH 8.0) and disrupted by sonication. Supernatants were collected by centrifugation at 45,000 g for 1 h and applied to Ni-NTA resin that had been pre-equilibrated with lysis buffer. The Ni-NTA column was washed with 5 column volumes of wash buffer (50 mM Tris-HCl, 2 mM DTT, 30 mM imidazole and 150 mM NaCl, pH 8.0), and eluted with 5 column volumes of elution buffer (50 mM Tris-HCl, 2 mM DTT, 300 mM imidazole, pH 8.0). The resulting eluent was filtered and further purified by anion exchange chromatography (HiTrapQ, GE Healthcare). A linear gradient from 0-1 M NaCl in buffer A (50 mM Tris-HCl, 2 mM DTT, pH 8.0) was used to purify each protein. Freshly purified proteins were frozen and stored at −80° C. until use.

LpxB, LpxH and LpxK are membrane-associated proteins. They were also expressed in *E. coli* BL21(DE3). Due to the cytotoxicity resulting from membrane protein overexpression, 1% (w/v) glucose was supplemented in culture media during the growth phase of each cell line. Cells were harvested in a similar fashion to the protocol described above. In order to screen different types of detergent for solubilization, 50 mM Tris was substituted with 20 mM HEPES in all buffers while other buffer components remained the same. To extract LpxB, cells were resuspended in lysis buffer containing 0.2% Triton X-100, and disrupted by sonication. Supernatants was collected by centrifugation at 45,000 g for 1 h, and applied to Ni-NTA resin pre-equilibrated with lysis buffer. Wash and elution buffers also contained 0.1% TritonX-100 to prevent LpxB from aggregating. Anion exchange chromatography buffers were supplemented with 0.05% Triton X-100 for the same reason. Freshly purified proteins were frozen and stored at −80° C. until use.

The cell line expressing LpxH was grown and induced as above. Cells were harvested after overnight protein expression, washed with PBS and stored at −80° C. Cells harboring the LpxK expression plasmid were grown at 37° C., and induced at the same temperature with 1 mM IPTG when the OD$_{600}$ reached 0.6. After culturing for an additional 3-5 h, cells were harvested, washed with PBS and stored in −80° C. Cell pellets were then thawed at 4° C. and resuspended in lysis buffer without NaCl. After sonication, the cell debris was removed by centrifugation at 10,000 g for 45 min. The supernatant was collected, and subjected to ultracentrifugation at 150,000 g for 1 h to collect the membrane fraction. Solubilizing buffer (20 mM HEPES, 2 mM DTT, 10 mM imidazole, 150 mM NaCl, 2% Triton X-100, pH 8.0) was carefully added and gently pipetted to resuspend the pelleted membrane. The resulting cloudy mixture was incubated on a roller for 1 h. The extracted membrane fraction was removed by ultracentrifugation at 250,000 g for 1 h. The supernatant was applied to Ni-NTA resin pre-equilibrated with lysis buffer and 1% Triton X-100. Ni-NTA wash and elution buffers were supplemented with 0.5% Triton X-100, and anion-exchange chromatography buffers were contained 0.05% Triton X-100. Freshly purified proteins were frozen and stored at −80° C. until use.

Frozen proteins were then buffer exchanged into 100 mM sodium phosphate buffer, pH 7.5, using PD-10 columns (GE healthcare) and following the manufacturer's instructions. Protein concentrations were measured by BCA assay (Thermo Scientific), and aliquots were stored at −80° C. until use.

Structural analysis of Lipid IV$_A$, its pathway intermediates, and its analogs. In vitro reaction mixtures containing Lipid IV$_A$, its pathway intermediates, and its analogs were analyzed on an Agilent 1290 Infinity Quaternary LC System interfaced with a Sciex TripleTOF 6600, a hybrid triple quadrupole time-of-flight mass spectrometer fitted with a Turbo V ion source.

A mixed-mode liquid chromatography separation protocol (anion-exchange/normal phase) was used to separate these glycolipids. Specifically, a BioBasic AX column (5 μm, 2.1 mm×50 mm, Thermo Scientific) was used. Lyophilized samples were dissolved in methanol, and 10 μL aliquots were injected. Mobile phase A consisted of 20:80 water/acetonitrile with 10 mM ammonium acetate, whereas mobile phase B consisted of 50:50 water/acetonitrile with 0.1% ammonium hydroxide. The gradient was held at 0% B for 0.5 min, followed by a linear ramp to 100% B over 6 min. It was then held at 100% B for 1 min, followed by another linear ramp to 0% B over 0.1 min and maintenance at 0% B for 1.4 min to allow the column to re-equilibrate. The LC flow rate was 600 μL/min.

Mass spectra were acquired in negative ion mode using an ion spray voltage of −4.5 kV, curtain gas at 30 psi, nebulizer gas at 60 psi, declustering energy of −50 V, and an interface heater temperature of 600° C. A collision energy sweep setting of −35±15 V was applied to all precursor ions. Data was processed using PeakView v2.2 and MultiQuant 3.02 software.

Identification and quantitation of acyl-ACP intermediates. In vitro reaction mixtures containing acyl-ACP intermediates were analyzed on an Agilent 1290 Infinity Quaternary LC System interfaced with a Sciex TripleTOF 6600, a hybrid triple quadrupole time-of-flight mass spectrometer fitted with a Turbo V ion source.

A reverse-phase liquid chromatography column (Aeris WIDEPORE XB-C$_8$, 3.6 μm, 2.1 mm×50 mm, Phenomenex) was used to separate these glycolipids. Lyophilized samples were dissolved in 10% acetonitrile, and 10 μL aliquots were injected. Mobile phase A consisted of water plus 0.1% formic acid, whereas mobile phase B consisted of acetonitrile plus 0.1% formic acid. The gradient was held at 0% B for 0.5 min, followed by a linear ramp to 100% B over 6 min. It was then held at 100% B for 1 min, followed by another linear ramp to 0% B over 0.1 min and maintenance at 0% B for 1.4 min to allow the column to re-equilibrate. The LC flow rate was 600 μL/min.

Mass spectra were acquired in negative ion mode using an ion spray voltage of 5.5 kV, curtain gas at 25 psi, nebulizer gas at 60 psi, declustering energy of 80 V, and an interface heater temperature of 500° C. SWATH experiments were set to engage a 3 amu step up from m/z of 832.8 to 852.3 (corresponding to the most abundant multiply charged ACP ion over with mass ranging from holo-ACP to arachidyl-ACP). A collision energy sweep setting of 30±10 V was applied to SWATH precursor ions. Data was processed using PeakView v2.2 and MultiQuant 3.02 software.

TLR Signaling Assays. HUVECs were grown to approximately 80% confluency in plastic 48-well cell culture plates. Six hours prior to the beginning the assay, medium was aspirated and replaced with 200 μL fresh medium per well. 100× stock dilutions of LPS (in sterile water) and Lipid IVa (in methanol) were freshly prepared from lyophilized solids. Cells were subjected to a 1-hour preincubation with the indicated amounts of Lipid IVa, or Samples 1, 2, or 3, and then LPS (100 ng/mL) was added. Aliquots of the culture supernatant were taken after 18 hours, frozen at −20 C, and then analyzed for IL-6 using a commercial ELISA kit following the manufacturer's (eBioSciences) recommended protocol.

TABLE 3

Product ions in the ESI $MS^2$ spectrum of m/z 701.4214, corresponding to (fully saturated) lipid $IV_4$

| Composition | Intensity (%) | Theoretical Mass/Charge | Experimental Mass/Charge | Error (Da) |
|---|---|---|---|---|
| $C_{40}H_{74}N_2O_{15}P^-$ | 23.09 | 853.4832 | 853.4853 | 0.002 |
| $C_{54}H_{100}N_2O_{17}P^-$ | 12.80 | 1079.6765 | 1079.6772 | 0.005 |
| $C_{68}H_{128}N_2O_{20}P^-$ | 16.61 | 1323.8804 | 1323.8824 | 0.003 |

TABLE 4

Product ions in the ESI $MS^2$ spectrum of m/z 700.4122, correspond to a lipid $IV_4$ analog with one mono-unsaturated fatty acyl chain

| Composition | Intensity (%) | Theoretical Mass/Charge | Experimental Mass/Charge | Error (Da) |
|---|---|---|---|---|
| $C_{40}H_{72}N_2O_{15}P^-$ | 16.81 | 851.4676 | 851.4692 | 0.002 |
| $C_{54}H_{98}N_2O_{17}P^-$ | 10.68 | 1077.6609 | 1077.6608 | <0.001 |
| $C_{68}H_{126}N_2O_{20}P^-$ | 22.27 | 1321.8547 | 1321.8587 | 0.006 |

TABLE 5

Product ions in the ESI $MS^2$ spectrum of m/z 699.4061, correspond to a lipid $IV_4$ analog with two mono-unsaturated fatty acyl chains

| Composition | Intensity (%) | Theoretical Mass/Charge | Experimental Mass/Charge | Error (Da) |
|---|---|---|---|---|
| $C40•H72•N2•O15•P-$ | 16.88 | 851.4676 | 851.4665 | 0.001 |
| $C54•H96•N2•O17•P-$ | 7.26 | 1075.6452 | 1075.6463 | 0.001 |
| $C68•H124•N2•O20•P-$ | 13.42 | 1319.8491 | 1319.8479 | 0.001 |

TABLE 6

Product ions in the ESI $MS^2$ spectrum of m/z 698.3957, correspond to a lipid $IV_4$ analog with three mono-unsaturated fatty acyl chains

| Composition | Intensity (%) | Theoretical Mass/Charge | Experimental Mass/Charge | Error (Da) |
|---|---|---|---|---|
| $C_{40}H_{70}N_2O_{15}P^-$ | 14.71 | 849.4519 | 849.4526 | 0.001 |
| $C_{54}H_{96}N_2O_{17}P^-$ | 10.49 | 1075.6452 | 1075.6383 | 0.007 |
| $C_{68}H_{122}N_2O_{20}P^-$ | 21.36 | 1317.8334 | 1317.8279 | 0.006 |

TABLE 7

Product ions in the ESI $MS^2$ spectrum of m/z 697.3913, correspond to a lipid $IV_4$ analog with four mono-unsaturated fatty acyl chains

| Composition | Intensity (%) | Theoretical Mass/Charge | Experimental Mass/Charge | Error (Da) |
|---|---|---|---|---|
| $C_{40}H_{70}N_2O_{15}P^-$ | 20.07 | 849.4519 | 849.4535 | 0.002 |
| $C_{54}H_{94}N_2O_{17}P^-$ | 11.26 | 1073.6292 | 1073.6323 | 0.003 |
| $C_{68}H_{122}N_2O_{20}P^-$ | 16.90 | 1315.8187 | 1315.8201 | 0.002 |

TABLE 8

MRM ion pairs of stearyl-ACP ($C_{18:0}$), oleyl-ACP ($C_{18:1}$)

| Acyl-ACP | Precursor Range M/Z | Ppant Ejection Formula | Theoretical M/Z |
|---|---|---|---|
| $C_{18:1}$ | 850.5-853.5 | C29H53N2O4S+ | 525.3721 |
| $C_{18:0}$ | 850.5-853.5 | C29H55N2O4S+ | 527.3877 |

TABLE 9

MRM ion pairs of arachidyl-ACP ($C_{20:0}$) and gondoyl-ACP ($C_{20:1}$)

| Acyl-ACP | Precursor Range M/Z | Ppant Ejection Formula | Theoretical M/Z |
|---|---|---|---|
| $C_{20:1}$ | 852.3-855.3 | C31H57N2O4S+ | 553.4034 |
| $C_{20:0}$ | 852.3-855.3 | C31H59N2O4S+ | 555.4190 |

TABLE 10

HUVEC cell culture supernatant levels of human IL-6 as assessed by ELISA. Cells were pretreated with the indicated amounts of compound for 1 hour and then dosed with 100 ng/mL LPS. The levels of IL-6 in the culture supernatant 18 hours after LPS treatment was assessed by ELISA. Values reported are the mean ± standard deviation of triplicate wells.

| Compound | [IL-6] (pg/mL) |
|---|---|
| None | 425 ± 7 |
| 10 ng/mL Lipid $IV_A$ | 484 ± 25 |
| 100 ng/mL Lipid $IV_A$ | 212 ± 33 |
| 500 ng/mL Lipid $IV_A$ | 57 ± 3 |
| 10 ng/mL Sp1 | 459 ± 83 |
| 100 ng/mL Sp1 | 331 ± 25 |
| 500 ng/mL Sp1 | 51 ± 2 |
| 10 ng/mL Sp2 | 474 ± 91 |
| 100 ng/mL Sp2 | 313 ± 98 |
| 500 ng/mL Sp2 | 96 ± 34 |
| 10 ng/mL Sp3 | 547 ± 72 |
| 100 ng/mL Sp3 | 285 ± 23 |
| 500 ng/mL Sp3 | 74 ± 7 |
| Negative Control | 517 ± 114 |

What is claimed is:

1. A method of synthesizing a compound represented by one of the following structures:

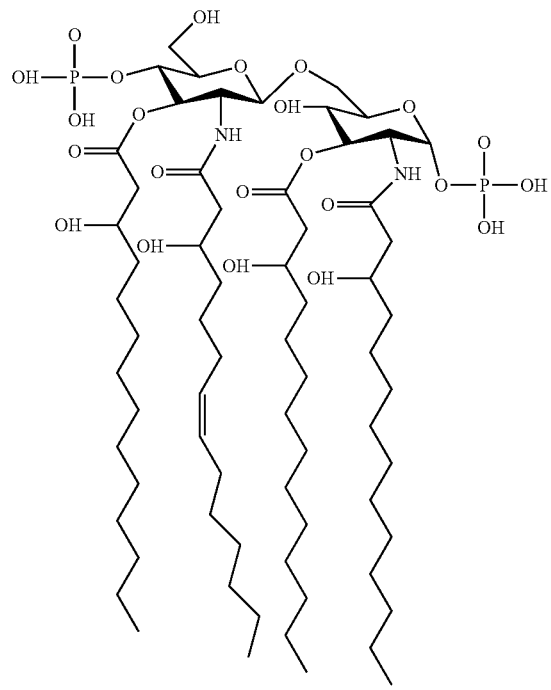

6b

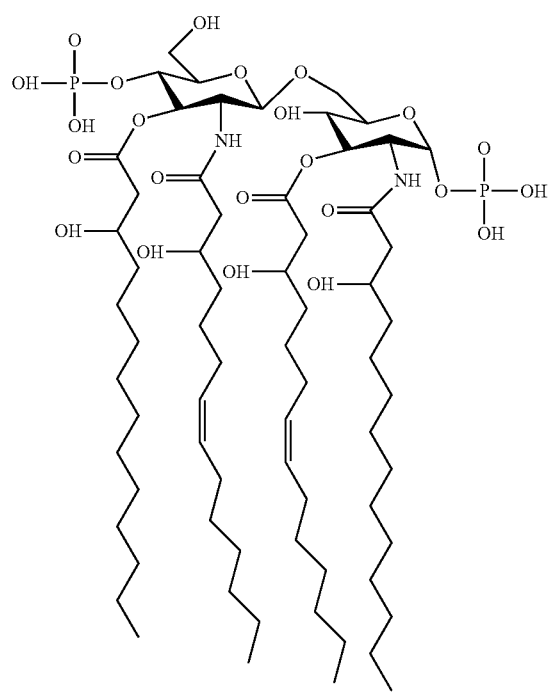

6c

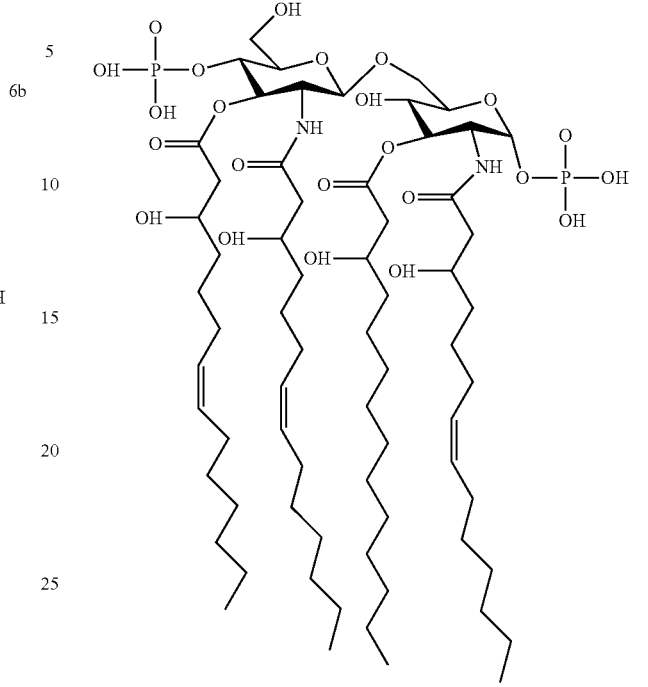

6d

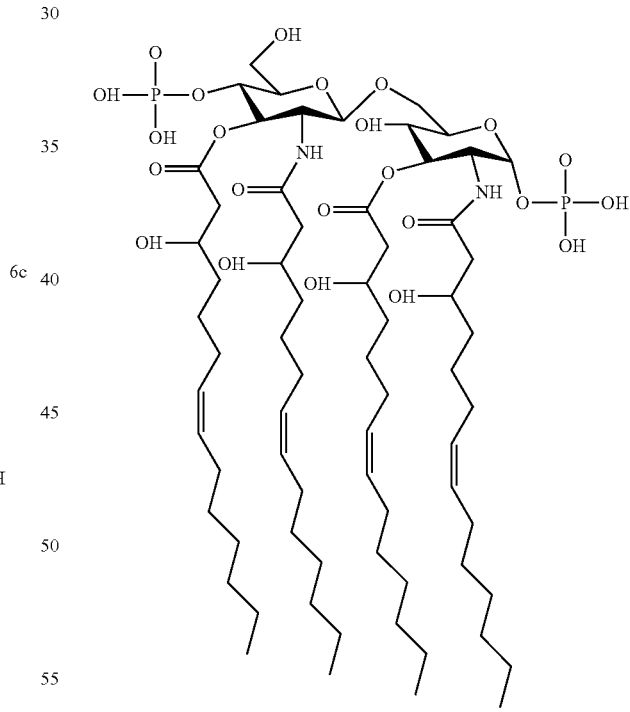

6e the method comprising:
 combining in a reaction mixture each of the following sets of enzymes:
 Module A: Acetyl-CoA carboxylases;
 Module B: chain initiation enzymes of fatty acid synthases;
 Module C: chain elongation enzymes of fatty acid synthases;
 Module D: Lipid A biosynthetic enzymes; in the presence of Acetyl-coenzyme A (CoA) or an analog thereof including, UDP-N-acetyl-D-glucosamine (GlcNAc), and cofactors and buffers required for synthesis.
2. A method of synthesizing a compound represented by one of the following structures:
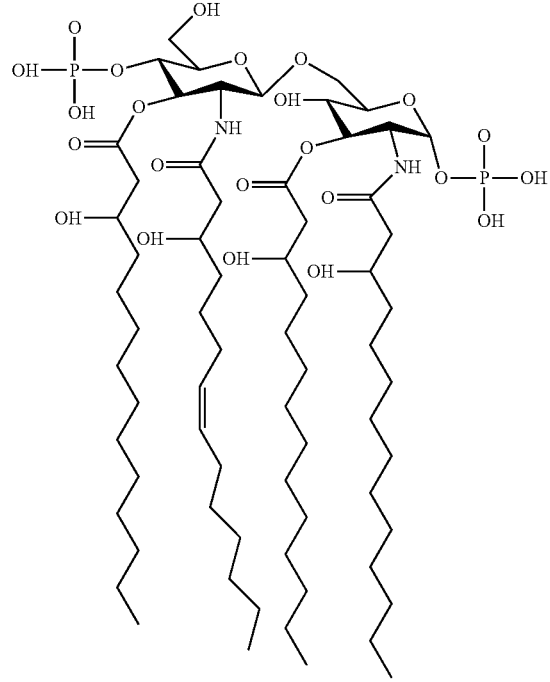
6b
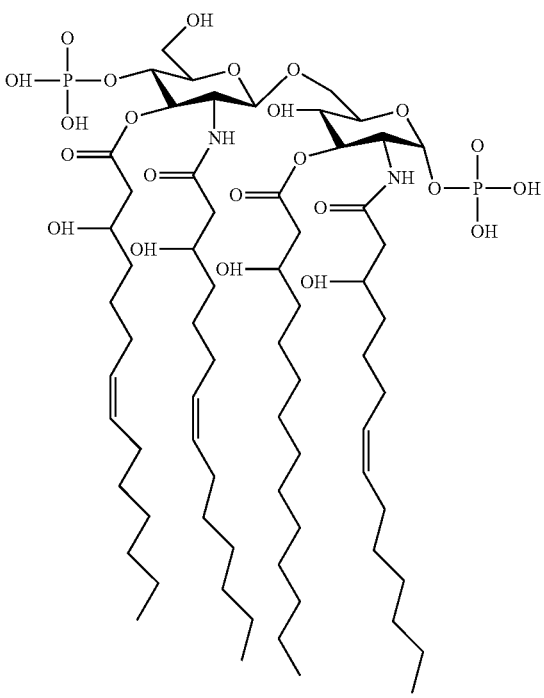
6d
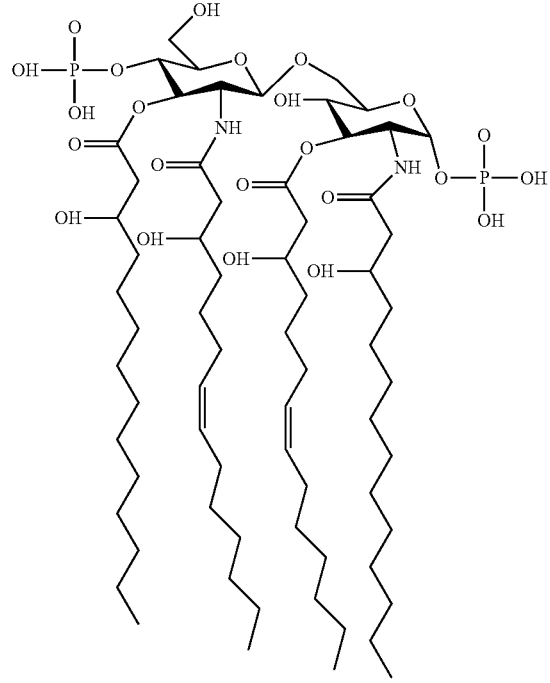
6c
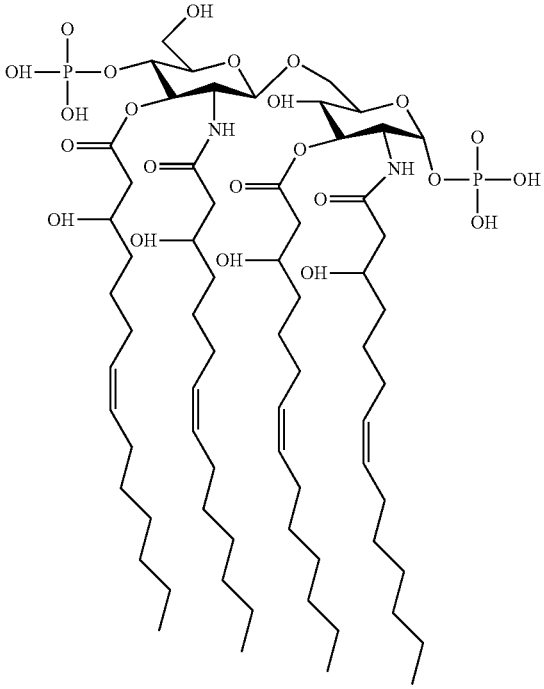
6e the method comprising:

combining in a reaction mixture the following sets of enzymes:

Module A, comprised of Acetyl-CoA carboxylase C (AccC), Acetyl-CoA carboxylase A (AccA), Acetyl-CoA carboxylase D (AccD), and holo-Acetyl-CoA carboxylase B (AccB); Module B comprised of Fatty Acid Biosynthesis H (FabH), Fatty Acid Biosynthesis D (FabD), Fatty Acid Biosynthesis G (FabG), Fatty Acid Biosynthesis A (FabA) or Fatty Acid Biosynthesis Z (FabZ), Fatty Acid Biosynthesis I (FabI), and holo-Acyl Carrier Protein (ACP); Module C, comprised of Fatty Acid Biosynthesis B (FabB) or Fatty Acid Biosynthesis F (FabF), FabD, FabG, FabA or FabZ, and FabI; and Module D, comprised of UDP-N-acetylglucosamine acyltransferase (LpxA), UDP-3-O-acyl-N-acetylglucosamine deacetylase (LpxC), UDP-3-O-(3-hydroxymyristoyl)glucosamine N-acyltransferase UDP-2,3-diacylglucosamine hydrolase (LpxH), Lipid-A-disaccharide synthase (LpxB), and tetraacyldisaccharide 4'-kinase (LpxK), in the presence of Acetyl-CoA or an analog thereof including, UDP-GlcNAc, and cofactors and buffers required for synthesis.

3. A method of synthesizing a compound represented by one of the following structures:

-continued

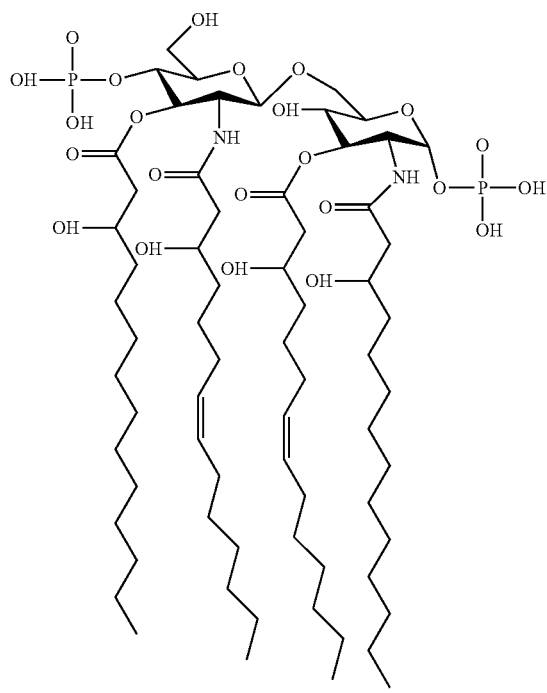

6c

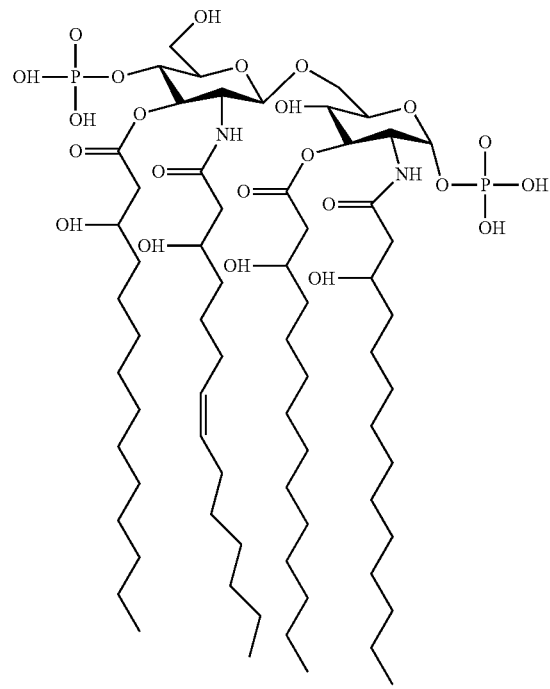

6b

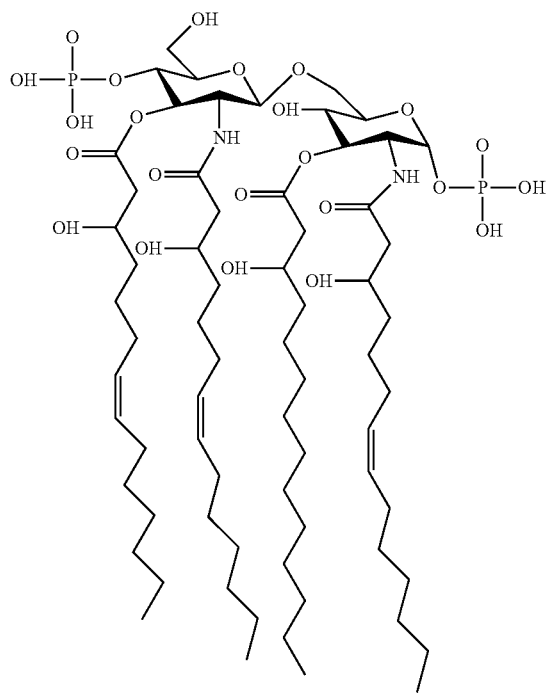

6d

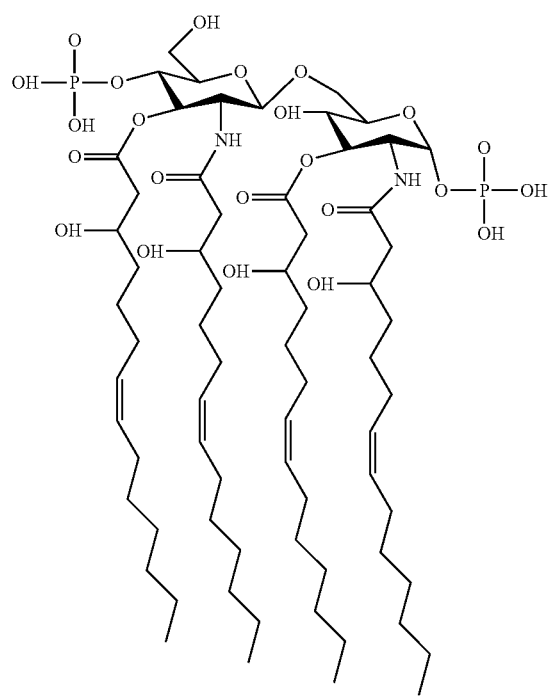

6e

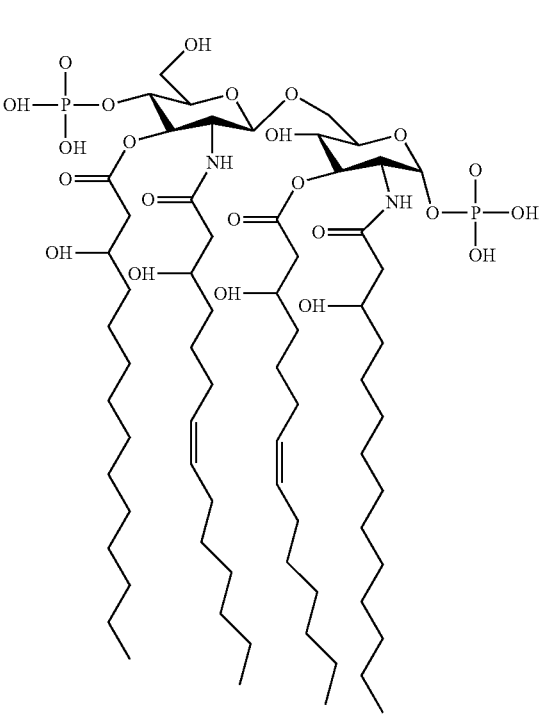

6c the method comprising:
  combining in a reaction mixture the following sets of enzymes:
  Module B comprised of FabH, FabD, FabG, FabA or FabZ, FabI, and holo-ACP; Module C, comprised of FabB or FabF, FabD, FabG, FabA or FabZ, and FabI; and Module D, comprised of LpxA, LpxC, LpxD, LpxH, LpxB, and LpxK, in the presence of malonyl-CoA, Acetyl-CoA or an analog thereof including, UDP-GlcNAc, and cofactors and buffers required for synthesis.

4. A method of synthesizing a compound represented by one of the following structures:

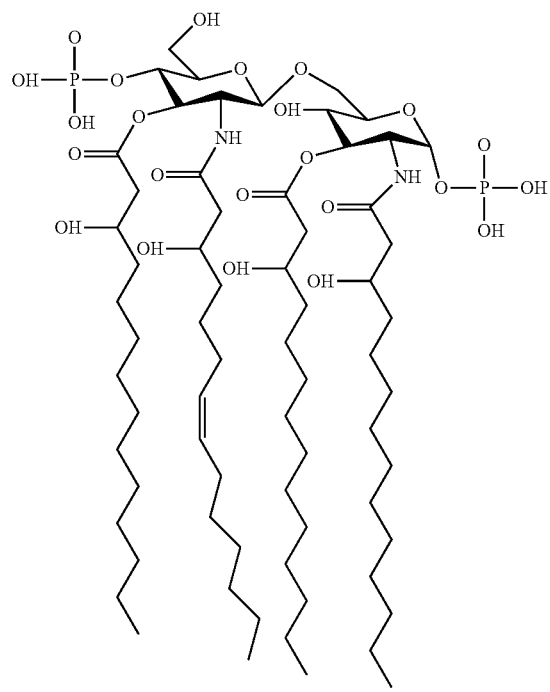

6b

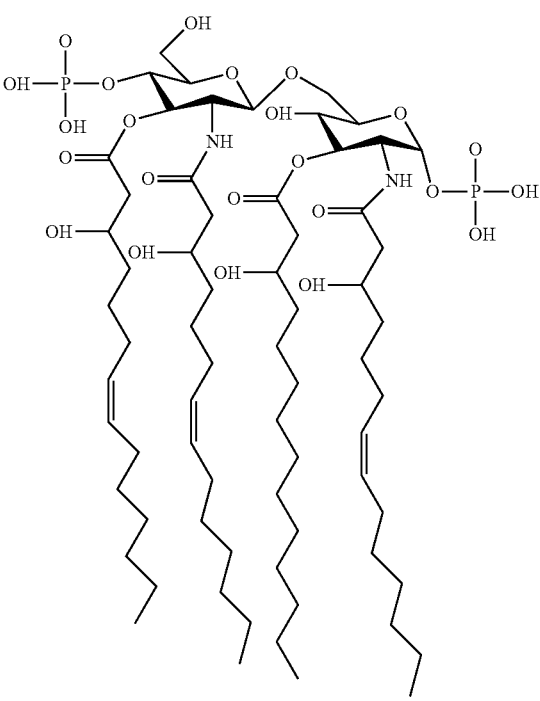

6d

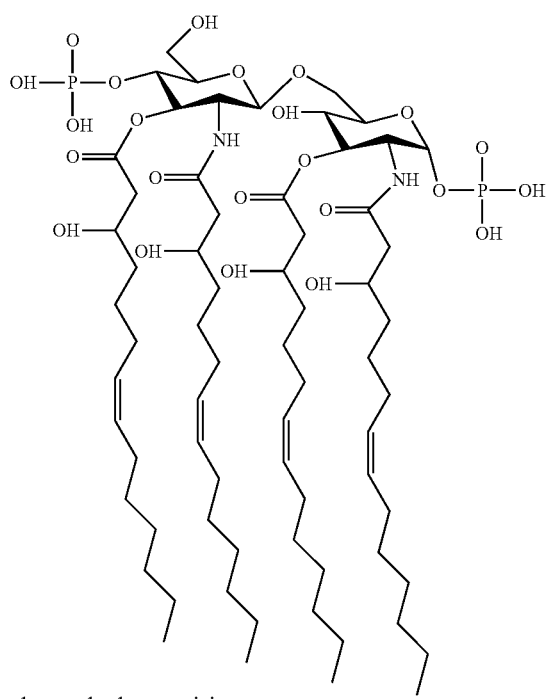

6e

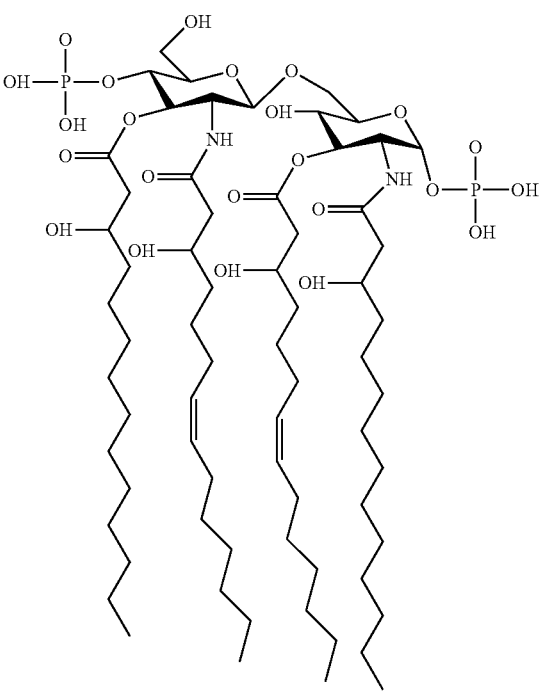

6c the method comprising:
combining in a reaction mixture the following sets of enzymes:
Module C, comprised of FabB or FabF, FabD, FabG, FabA or FabZ, and FabI; and Module D, comprised of LpxA, LpxC, LpxD, LpxH, LpxB, and LpxK, in the presence of butyryl-ACP thioester, malonyl-CoA, UDP-GlcNAc, and cofactors and buffers required for synthesis.

5. A method of synthesizing a compound represented by one of the following structures:

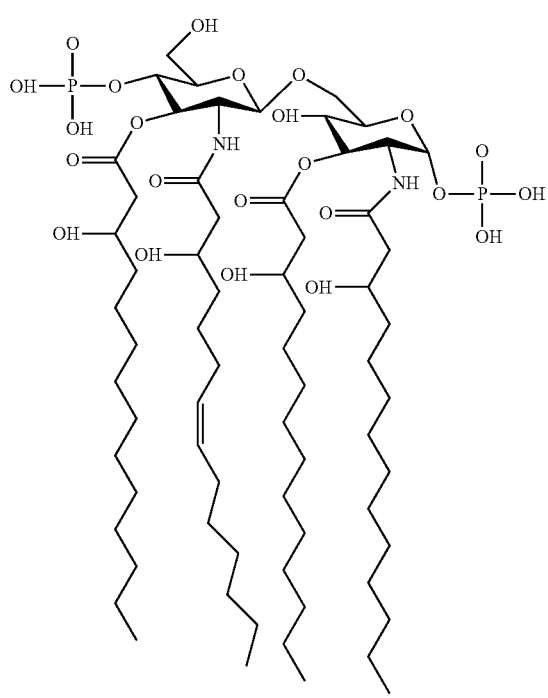

6b

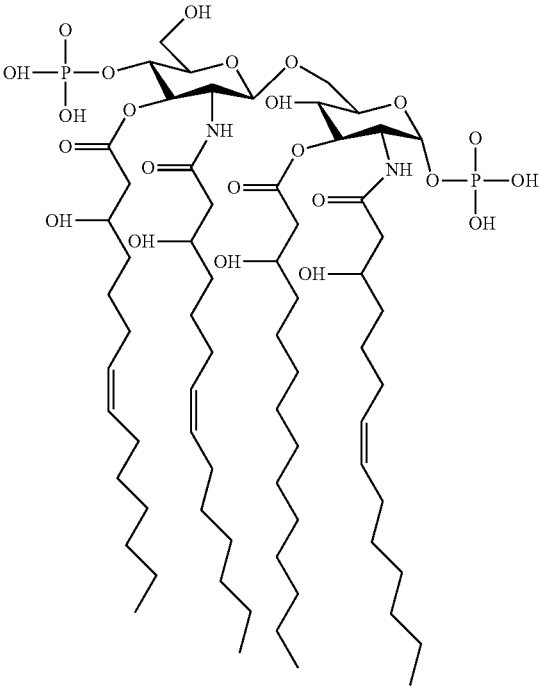

6d

-continued

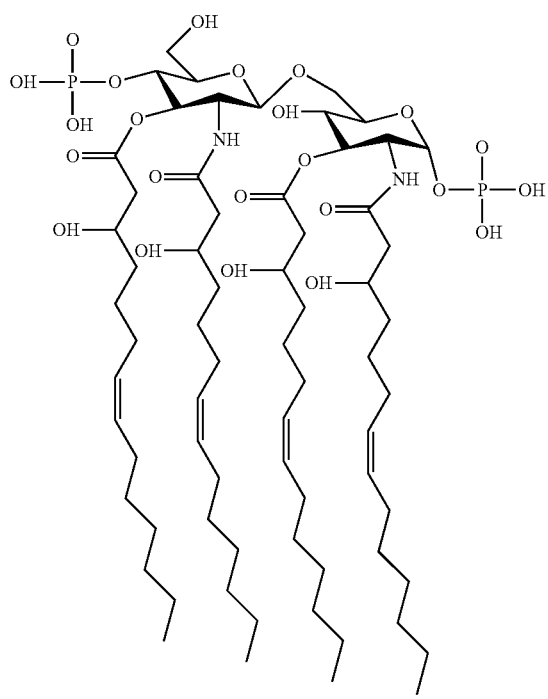

6e the method comprising:
combining in a reaction mixture the following set of enzymes:
Module D, comprised of LpxA, LpxC, LpxD, LpxH, LpxB, and LpxK, in the presence of 3-hydroxy-myristoyl-ACP intermediate and UDP-N-acetylglucosamine (UDP-GlcNAc), and cofactors and buffers required for synthesis.

6. The method according to claim 1, wherein the reaction mixture is cell-free.

7. The method according to claim 1 wherein each enzyme is from the same organism.

8. The method according to claim 1, wherein one or more enzyme is from a different organism.

9. The method of claim 8 wherein at least one enzyme is selected from an enzyme corresponding to UniProt Entry P0AC75; D5VD80; Q2K2U9; B2RLI7; Q9ZN40; Q2KA78; B2RI48; Q9ZJ31; Q8A6M3; P0ACV0; D5VBR7; G9Y3H2; C2LFR4; C2LM44; A0A0B6NZY9; P24205; G9Y294; Q7CIC3; Q9X6P4; O25927; Q3BDJ0; Q9HXY6; O24991; D5VAW6; P76445; Q0QMQ4; Q9HVD1; P37001; B4EYA9; P76473; Q9HY61; P30845; A0A0E1EWJ6; P37661; Q4FAC7; Q20DQ4; Q20DQ3; and Q20DQ2.

10. The method of claim 7, wherein synthesis is performed in a cell.

11. The method of claim 1, wherein the enzymes are provided in the molar ratios 10:5:1, holo-AccB and ho/o-ACP:Module D enzymes:all other enzymes.

12. The method of claim 1, wherein a molar excess is provided of at least about 2-fold or more of the Module D enzymes in relation to the Module A, B and C enzymes when present except holo-AccB and holo-ACP, which are provided in a molar ratio equivalent to the Module D enzymes, or in excess of the Module D enzymes.

13. The method of claim 1, 2 or 3, wherein the acetyl-coenzyme A analog is valeryl-CoA.

* * * * *

SEQUENCE LISTING

<160> NUMBER OF SEQ ID NOS: 20

<210> SEQ ID NO 1
<211> LENGTH: 32
<212> TYPE: DNA
<213> ORGANISM: Artificial Sequence
<220> FEATURE:
<223> OTHER INFORMATION: Synthetic nucleotide

<400> SEQUENCE: 1

```
atatatcata tgattgataa atccgccttt gt                                    32

<210> SEQ ID NO 2
<211> LENGTH: 42
<212> TYPE: DNA
<213> ORGANISM: Artificial sequence
<220> FEATURE:
<223> OTHER INFORMATION: Synthetic nucleotide

<400> SEQUENCE: 2
atatatgaat tcatgggcta ctagttaacg aatcagaccg cg                         42

<210> SEQ ID NO 3
<211> LENGTH: 34
<212> TYPE: DNA
<213> ORGANISM: Artificial sequence
<220> FEATURE:
<223> OTHER INFORMATION: Synthetic nucleotide

<400> SEQUENCE: 3
atatatcata tgatcaaaca aaggacactt aaac                                  34

<210> SEQ ID NO 4
<211> LENGTH: 29
<212> TYPE: DNA
<213> ORGANISM: Artificial sequence
<220> FEATURE:
<223> OTHER INFORMATION: Synthetic nucleotide

<400> SEQUENCE: 4
atatatctcg agtgccagta cagctgaag                                        29

<210> SEQ ID NO 5
<211> LENGTH: 30
<212> TYPE: DNA
<213> ORGANISM: Artificial sequence
<220> FEATURE:
<223> OTHER INFORMATION: Synthetic nucleotide

<400> SEQUENCE: 5
atatatgcta gcatgccttc aattcgactg                                       30

<210> SEQ ID NO 6
<211> LENGTH: 46
<212> TYPE: DNA
<213> ORGANISM: Artificial sequence
<220> FEATURE:
<223> OTHER INFORMATION: Synthetic nucleotide

<400> SEQUENCE: 6
atatatgaat tcatgggcta ctagttagtc ttgttgatta accttg                     46

<210> SEQ ID NO 7
<211> LENGTH: 32
<212> TYPE: DNA
<213> ORGANISM: Artificial sequence
<220> FEATURE:
<223> OTHER INFORMATION: Synthetic nucleotide

<400> SEQUENCE: 7
atatatcata tggcgacact ctttattgca ga                                    32

<210> SEQ ID NO 8
<211> LENGTH: 29
<212> TYPE: DNA
```

<213> ORGANISM: Artificial sequence
<220> FEATURE:
<223> OTHER INFORMATION: Synthetic nucleotide

<400> SEQUENCE: 8
atatatctcg agaaacggaa aatgaatca                               29

<210> SEQ ID NO 9
<211> LENGTH: 32
<212> TYPE: DNA
<213> ORGANISM: Artificial sequence
<220> FEATURE:
<223> OTHER INFORMATION: Synthetic nucleotide

<400> SEQUENCE: 9
atatatcata tgactgaaca gcgtccatta ac                           32

<210> SEQ ID NO 10
<211> LENGTH: 29
<212> TYPE: DNA
<213> ORGANISM: Artificial sequence
<220> FEATURE:
<223> OTHER INFORMATION: Synthetic nucleotide

<400> SEQUENCE: 10
atatatctcg agttgtgcta actccagaa                               29

<210> SEQ ID NO 11
<211> LENGTH: 32
<212> TYPE: DNA
<213> ORGANISM: Artificial sequence
<220> FEATURE:
<223> OTHER INFORMATION: Synthetic nucleotide

<400> SEQUENCE: 11
atatatcata tgatcgaaaa aatctggtct gg                           32

<210> SEQ ID NO 12
<211> LENGTH: 29
<212> TYPE: DNA
<213> ORGANISM: Artificial sequence
<220> FEATURE:
<223> OTHER INFORMATION: Synthetic nucleotide

<400> SEQUENCE: 12
atatatctcg aggttgccag aagccagca                               29

<210> SEQ ID NO 13
<211> LENGTH: 32
<212> TYPE: DNA
<213> ORGANISM: Artificial sequence
<220> FEATURE:
<223> OTHER INFORMATION: Synthetic nucleotide

<400> SEQUENCE: 13
atatatcata tggataaaat aaatgcggta at                           32

<210> SEQ ID NO 14
<211> LENGTH: 26
<212> TYPE: DNA
<213> ORGANISM: Artificial sequence
<220> FEATURE:
<223> OTHER INFORMATION: Synthetic nucleotide

<400> SEQUENCE: 14
atatatctcg agcgcatctt ctttgg                                  26

<210> SEQ ID NO 15
<211> LENGTH: 32
<212> TYPE: DNA
<213> ORGANISM: Artificial sequence
<220> FEATURE:
<223> OTHER INFORMATION: Synthetic nucleotide

<400> SEQUENCE: 15
atatatgcta gcatggaaaa aataaatgca gt                                    32

<210> SEQ ID NO 16
<211> LENGTH: 40
<212> TYPE: DNA
<213> ORGANISM: Artificial sequence
<220> FEATURE:
<223> OTHER INFORMATION: Synthetic nucleotide

<400> SEQUENCE: 16
atatatgaat tcatgggcta ctagttacga ttccttttt                             40

<210> SEQ ID NO 17
<211> LENGTH: 32
<212> TYPE: DNA
<213> ORGANISM: Artificial sequence
<220> FEATURE:
<223> OTHER INFORMATION: Synthetic nucleotide

<400> SEQUENCE: 17
atatatcata tggtaagtcc tctagcgtat at                                    32

<210> SEQ ID NO 18
<211> LENGTH: 40
<212> TYPE: DNA
<213> ORGANISM: Artificial sequence
<220> FEATURE:
<223> OTHER INFORMATION: Synthetic nucleotide

<400> SEQUENCE: 18
atatatgaat tcatgggcta ctagttattt aataatacca                            40

<210> SEQ ID NO 19
<211> LENGTH: 32
<212> TYPE: DNA
<213> ORGANISM: Artificial sequence
<220> FEATURE:
<223> OTHER INFORMATION: Synthetic nucleotide

<400> SEQUENCE: 19
atatatcata tggagttctc ggctaagcaa at                                    32

<210> SEQ ID NO 20
<211> LENGTH: 40
<212> TYPE: DNA
<213> ORGANISM: Artificial sequence
<220> FEATURE:
<223> OTHER INFORMATION: Synthetic nucleotide

<400> SEQUENCE: 20
atatatgaat tcatgggcta ctagttactt atttaatagt                            40